US010561728B2

(12) United States Patent
Reimann et al.

(10) Patent No.: US 10,561,728 B2
(45) Date of Patent: Feb. 18, 2020

(54) POLYNUCLEOTIDES ENCODING ANTI-CD40 ANTIBODIES

(71) Applicants: Beth Israel Deaconess Medical Center, Inc., Boston, MA (US); Emory University, Atlanta, GA (US)

(72) Inventors: Keith A. Reimann, Marblehead, MA (US); Rijian Wang, Saugus, MA (US); Christian P. Larsen, Atlanta, GA (US)

(73) Assignees: Beth Israel Deaconess Medical Center, Inc., Boston, MA (US); Emory University, Atlanta, GA (US)

( * ) Notice: Subject to any disclaimer, the term of this patent is extended or adjusted under 35 U.S.C. 154(b) by 0 days.

(21) Appl. No.: 15/991,432

(22) Filed: May 29, 2018

(65) Prior Publication Data

US 2018/0344845 A1    Dec. 6, 2018

Related U.S. Application Data

(62) Division of application No. 14/004,552, filed as application No. PCT/US2012/028782 on Mar. 12, 2012, now Pat. No. 9,987,356.

(60) Provisional application No. 61/451,870, filed on Mar. 11, 2011.

(51) Int. Cl.
    *C12N 15/13*    (2006.01)
    *C12N 15/12*    (2006.01)
    *C12N 15/63*    (2006.01)
    *A61K 39/395*   (2006.01)
    *A61K 38/13*    (2006.01)
    *A61K 45/06*    (2006.01)
    *A61K 31/436*   (2006.01)
    *C07K 16/28*    (2006.01)
    *A61P 37/06*    (2006.01)
    *C07K 16/18*    (2006.01)
    *A61K 39/00*    (2006.01)

(52) U.S. Cl.
    CPC ........ *A61K 39/3955* (2013.01); *A61K 31/436* (2013.01); *A61K 38/13* (2013.01); *A61K 39/39541* (2013.01); *A61K 45/06* (2013.01); *A61P 37/06* (2018.01); *C07K 16/18* (2013.01); *C07K 16/2866* (2013.01); *C07K 16/2875* (2013.01); *C07K 16/2878* (2013.01); *A61K 2039/505* (2013.01); *A61K 2039/507* (2013.01); *C07K 2317/24* (2013.01); *C07K 2317/33* (2013.01); *C07K 2317/76* (2013.01); *Y02A 50/386* (2018.01); *Y02A 50/41* (2018.01); *Y02A 50/412* (2018.01); *Y02A 50/414* (2018.01); *Y02A 50/423* (2018.01)

(58) Field of Classification Search
    None
    See application file for complete search history.

(56) References Cited

U.S. PATENT DOCUMENTS

| | | |
|---|---|---|
| 5,225,539 A | 7/1993 | Winter |
| 5,677,165 A | 10/1997 | de Boer et al. |
| 5,693,761 A | 12/1997 | Queen et al. |
| 5,693,762 A | 12/1997 | Queen et al. |
| 5,801,227 A | 9/1998 | Fanslow, III et al. |
| 5,874,082 A | 2/1999 | de Boer |
| 6,004,552 A | 12/1999 | de Boer et al. |
| 6,051,228 A | 4/2000 | Aruffo et al. |
| 6,054,297 A | 4/2000 | Carter et al. |
| 6,056,959 A | 5/2000 | de Boer et al. |
| 6,132,978 A | 10/2000 | Gelfand et al. |
| 6,280,957 B1 | 8/2001 | Sayegh et al. |
| 6,312,693 B1 | 11/2001 | Aruffo et al. |
| 6,315,998 B1 | 11/2001 | de Boer et al. |
| 6,413,514 B1 | 7/2002 | Aruffo et al. |
| 6,632,927 B2 | 10/2003 | Adair et al. |
| 7,063,845 B2 | 6/2006 | Mikayama et al. |
| 7,193,064 B2 | 3/2007 | Mikayama et al. |
| 7,288,251 B2 | 10/2007 | Bedian et al. |
| 7,361,345 B2 | 4/2008 | de Boer et al. |
| 7,445,780 B2 | 11/2008 | Chu et al. |
| 7,498,032 B2 | 3/2009 | Siegall et al. |
| 7,537,763 B2 | 5/2009 | Mikayama et al. |
| 7,790,166 B2 | 9/2010 | de Boer et al. |
| 8,106,164 B2 | 1/2012 | Gellerfors et al. |
| 8,138,134 B2 | 3/2012 | Zhang et al. |
| 8,226,952 B2 | 7/2012 | Thomas, Jr. et al. |
| 8,277,810 B2 | 10/2012 | Long et al. |
| 8,303,955 B2 | 11/2012 | Presta et al. |
| 8,435,514 B2 | 5/2013 | Perrin et al. |
| 8,591,900 B2 | 11/2013 | Barrett et al. |
| 8,784,823 B2 | 7/2014 | Burkly et al. |
| 8,828,396 B2 | 9/2014 | Heusser et al. |
| 8,911,726 B2 | 12/2014 | Takahashi et al. |
| 9,023,360 B2 | 5/2015 | Takahashi et al. |
| 9,023,361 B2 | 5/2015 | Takahashi et al. |
| 9,125,893 B2 | 9/2015 | Endo et al. |
| 9,475,879 B2 | 10/2016 | Suri et al. |
| 9,598,494 B2 | 3/2017 | Takahashi et al. |
| 9,974,855 B2 | 5/2018 | Yu et al. |
| 9,987,356 B2 * | 6/2018 | Reimann .......... A61K 39/39541 |

(Continued)

FOREIGN PATENT DOCUMENTS

| | | |
|---|---|---|
| EP | 1297017 | 4/2003 |
| EP | 1682180 | 7/2006 |

(Continued)

OTHER PUBLICATIONS

First Examination Report for Australian Patent Application No. 2017216556, dated Nov. 30, 2018 (6 pages).

(Continued)

*Primary Examiner* — Phillip Gambel
(74) *Attorney, Agent, or Firm* — Clark & Elbing LLP

(57) ABSTRACT

The present invention relates to antibodies specific for a particular epitope on CD40 and antibodies that bind CD40 and have particular functional characteristics. The present invention also relates to fragments of these antibodies, uses of the antibodies for reduction or treatment of transplant rejection and graft-versus-host disease, and methods for making the antibodies.

17 Claims, 12 Drawing Sheets

Specification includes a Sequence Listing.

(56) References Cited

U.S. PATENT DOCUMENTS

| | | |
|---|---|---|
| 2002/0031512 A1 | 3/2002 | Pasch et al. |
| 2003/0211100 A1 | 11/2003 | Bedian et al. |
| 2004/0110226 A1 | 6/2004 | Lazar et al. |
| 2004/0120948 A1 | 6/2004 | Mikayama et al. |
| 2005/0118166 A1 | 6/2005 | Yellin et al. |
| 2007/0110754 A1 | 5/2007 | Long et al. |
| 2007/0190051 A1 | 8/2007 | Bedian et al. |
| 2007/0218060 A1 | 9/2007 | Long et al. |
| 2008/0085531 A1 | 4/2008 | Den Hartog et al. |
| 2009/0123466 A1 | 5/2009 | Mikayama et al. |
| 2009/0304706 A1 | 12/2009 | Lu et al. |
| 2009/0311268 A1 | 12/2009 | Thomas et al. |
| 2010/0098694 A1 | 4/2010 | Bedian et al. |
| 2010/0234578 A1 | 9/2010 | Mikayama et al. |
| 2010/0239575 A1 | 9/2010 | Banchereau et al. |
| 2011/0027276 A1 | 2/2011 | Bernett et al. |
| 2011/0243932 A1 | 10/2011 | Barrett et al. |
| 2012/0121585 A1 | 5/2012 | Heusser et al. |
| 2013/0323267 A1 | 12/2013 | Endo et al. |
| 2014/0093497 A1 | 4/2014 | Reimann et al. |
| 2018/0344845 A1 | 12/2018 | Reimann et al. |

FOREIGN PATENT DOCUMENTS

| | | |
|---|---|---|
| EP | 1707627 A1 | 10/2006 |
| EP | 1945260 | 7/2008 |
| EP | 1297017 B1 | 6/2012 |
| EP | 1945260 B1 | 10/2012 |
| JP | 2005-508176 A | 3/2005 |
| JP | 2007-513073 A | 5/2007 |
| JP | 2009-513712 A | 4/2009 |
| JP | 2011-503098 A | 1/2011 |
| WO | WO-01/98357 A2 | 12/2001 |
| WO | WO-03/040170 A2 | 5/2003 |
| WO | WO-2005/044307 A2 | 5/2005 |
| WO | WO-2005/044854 A2 | 5/2005 |
| WO | WO-2007/053661 A2 | 5/2007 |
| WO | WO-2007/053767 A1 | 5/2007 |
| WO | WO-2007/075326 A2 | 7/2007 |
| WO | WO-2008/118356 A2 | 10/2008 |
| WO | WO-2009/062054 A1 | 5/2009 |
| WO | WO-2010/065819 A1 | 6/2010 |
| WO | WO-2012/065950 A1 | 5/2012 |
| WO | WO-2012/111762 A1 | 8/2012 |
| WO | WO-2012/125569 A2 | 9/2012 |
| WO | WO-2014/121099 A1 | 8/2014 |
| WO | WO-2016/119909 A1 | 8/2016 |
| WO | WO-2016/126702 A1 | 8/2016 |
| WO | WO-2017/004006 A1 | 1/2017 |

OTHER PUBLICATIONS

Mohiuddin et al., "Role of anti-CD40 antibody-mediated costimulation blockade on non-Gal antibody production and heterotopic cardiac xenograft survival in a GTKO.hCD46Tg pig-to-baboon model," available in PMC Sep. 18, 2017, published in final edited form as: Xenotransplantation. 21(1): 35-45 (2014) (18 pages).

Mohiuddin et al., "Chimeric 2C10R4 anti-CD40 antibody therapy is critical for long-term survival of GTKO.hCD46.hTBM pig-to-primate cardiac xenograft," Nat Commun. 7:1138 (2016) (10 pages).

Lee et al., "In vitro testing of an anti-CD40 monoclonal antibody, clone 2C10, in primates and pigs," available in PMC Nov. 1, 2016, published in final edited form as: Transpl Immunol. 33(3):185-191 (2015) (17 pages).

Carpenter et al., "Activation of human B cells by the agonist CD40 antibody CP-870,893 and augmentation with simultaneous toll-like receptor 9 stimulation," J Transl Med. 7:93 (2009) (10 pages).

Yamniuk et al., "Functional Antagonism of Human CD40 Achieved by Targeting a Unique Species-Specific Epitope," J Mol Biol. 428(14):2860-79 (2016).

Chamberlain et al., "Repeated administration of dapirolizumab pegol in a randomised phase I study is well tolerated and accompanied by improvements in several composite measures of systemic lupus erythematosus disease activity and changes in whole blood transcriptomic profiles," Ann Rheum Dis. 76(11):1837-44 (2017) (9 pages).

Apexigen Inc., APX005M Briefing Materials, Oncologic Drugs Advisory Committee, Jun. 21, 2017 (22 pages).

Bankert et al., "Induction of an altered CD40 signaling complex by an antagonistic human monoclonal antibody to CD40," J Immunol. 194(9):4319-27 (2015).

Visvanathan et al., "Treatment with BI 655064 (Antagonistic Anti-CD40 Antibody) Modulates Clinical and Biomarker Parameters Associated with Rheumatoid Arthritis (RA)," Scientific Abstracts, p. 517 Jun. 10, 2016.

Slade et al., "Assessment of Safety, Pharmacokinetics and Pharmacodynamics of a Novel Anti-CD40 Monoclonal Antibody, CFZ533, in Healthy Volunteers and in Rheumatoid Arthritis Patients," 2016 ACR/ARNP Annual Meeting, Nov. 11-16, Washington, DC. 68 (suppl 10), Abstract 1582 (2016).

Cooper et al., "Platelet-associated antibodies, cellular immunity and FCGR3a genotype influence the response to rituximab in immune thrombocytopenia," Br J Haematol. 158(4):539-47 (2012).

Cordoba et al., "A novel, blocking, Fc-silent anti-CD40 monoclonal antibody prolongs nonhuman primate renal allograft survival in the absence of B cell depletion," Am J Transplant. 15(11):2825-36 (2015).

Grammer et al., "Abnormal germinal center reactions in systemic lupus erythematosus demonstrated by blockade of CD154-CD40 interactions," J Clin Invest. 112(10):1506-20 (2003).

Kim et al., "Costimulation blockade alters germinal center responses and prevents antibody-mediated rejection," avilable in PMC Apr. 14, 2014, published in final edited form as :Am J Transplant. 14(1):59-69 (2014) (19 pages).

Kim et al., "Fc-Silent Anti-CD154 Domain Antibody Effectively Prevents Nonhuman Primate Renal Allograft Rejection," available in PMC May 1, 2018, published in final edited form as: Am J Transplant. 17(5):1182-92 (2017) (24 pages).

Kuwana et al., "Effect of a single injection of humanized anti-CD154 monoclonal antibody on the platelet-specific autoimmune response in patients with immune thrombocytopenic purpura," Blood. 103(4):1229-36 (2004).

Okimura et al., "Characterization of ASKP1240, a fully human antibody targeting human CD40 with potent immunosuppressive effects," Am J Transplant. 14(6):1290-99 (2014).

O'Neill et al,. "Comparative Evaluation of alphaCD40 (2C10R4) and alphaCD154 (5C8H1 and IDEC-131) in a Nonhuman Primate Cardiac Allotransplant Model," available in PMC Sep. 1, 2018, published in final edited form as: Transplantation. 101(9):2038-47 (2017) (22 pages).

Shock et al., "CDP7657, an anti-CD4OL antibody lacking an Fc domain, inhibits CD4OL-dependent immune responses without thrombotic complications: an in vivo study," Arthritis Res Ther. 17:234 (2015) (12 pages).

Daniluk et al., "SAT0147 Safety and Efficacy of BI 655064, An Antagonistic Anti-CD40 Antibody in Rheumatoid Arthritis (RA) Patients," Ann Rheum Dis. 75(suppl 2) (2016) (3 pages) (Abstract only).

Wu, Chapter 12: Simultaneous Humanization and Affinity Optimization of Monoclonal Antibodies. *Methods in Molecular Biology, vol. 207: Recombinant Antibodies for Cancer Therapy: Methods and Protocols*. Humana Press Inc., 197-212 (2003).

Schwabe et al., "FRI0168 Safety, Tolerability, Pharmacokinetics (PK) and Pharmacodynamics (PD) of BI 655064, An Antagonistic Anti-CD40 Antibody in Healthy Volunteers," Ann Rheum Dis. 74(suppl 2) (2015) (3 pages) (Abstract only).

Visvanathan et al., "FRI0231 Treatment with BI 655064 (Antagonistic Anti-CD40 Antibody) Modulates Biomarkers Associated with Rheumatoid Arthritis (RA)," Ann Rhem Dis. 75(suppl 2) (2016) (3 pages) (Abstract only).

Lazar et al., "A Molecular Immunology Approach to Antibody Humanization and Functional Optimization," Molecular Immunol. 44(8): 1986-98 (2007) (Abstract only).

(56) References Cited

OTHER PUBLICATIONS

Albach et al., "Safety, pharmacokinetics, and pharmacodynamics of single rising doses of BI 655064, an antagonistic anti-CD40 antibody in healthy subjects: a potential novel treatment for autoimmune disease," Eur J Clin Pharmacol. 74(2):161-169 (2018).
Adams et al., "Development of a chimeric anti-CD40 monoclonal antibody that synergizes with LEA29Y to prolong islet allograft survival," J Immunol. 174(1):542-50 (2005).
Aoyagi et al., "A human anti-CD40 monoclonal antibody, 4D11, for kidney transplantation in cynomolgus monkeys: induction and maintenance therapy," Am J Transplant. 9(8):1732-41 (2009).
Badell et al., "Nondepleting anti-CD40-based therapy prolongs allograft survival in nonhuman primates," Am J Transplant. 12(1):126-35 (2012).
Boon et al., "Preclinical assessment of anti-CD40 Mab 5D12 in cynomolgus monkeys," Toxicology. 174(1):53-65 (2002).
Boon et al., "Prevention of experimental autoimmune encephalomyelitis in the common marmoset (*Callithrix jacchus*) using a chimeric antagonist monoclonal antibody against human CD40 is associated with altered B cell responses," J Immunol. 167(5):2942-9 (2001).
Chen et al., "Enhancement and destruction of antibody function by somatic mutation: unequal occurrence is controlled by V gene combinatorial associations," EMBO J. 14(12):2784-94 (1995).
Colman, "Effects of amino acid sequence changes on antibody-antigen interactions," Res Immunol. 145(1):33-6 (1994).
Communication for European Application No. 12758099.1-1412, dated Aug. 26, 2014 (7 pages).
De Boer et al., "Generation of monoclonal antibodies to human lymphocyte cell surface antigens using insect cells expressing recombinant proteins," J Immunol Methods. 152(1):15-23 (1992).
Denton et al., "Central role for CD40/CD40 ligand (CD154) interactions in transplant rejection," Pediatr Transplant. 2(1):6-15 (1998). Abstract Only. Retrieved from <http://www.ncbi.nlm.nih.gov/pubmed/10084754> on Nov. 18, 2013
First Examination Report for Australian Patent Application No. 2012229236, dated May 4, 2016 (4 pages).
Gilson et al., "Anti-CD40 monoclonal antibody synergizes with CTLA4-lg in promoting long-term graft survival in murine models of transplantation," J Immunol. 183(3):1625-35 (2009).
Haanstra et al., "Prevention of kidney allograft rejection using anti-CD40 and anti-CD86 in primates." Transplantation. 75(5):637-43 (2003).
International Search Report and Written Opinion for International Applicaiton No. PCT/US2012/028782, dated Sep. 14, 2012 (11 pages).
Kussie et al., "A single engineered amino acid substitution changes antibody fine specificity," J Immunol. 152(1):146-52 (1994).
Liu et al., "Agonistic antibody to CD40 boosts the antitumor activity of adoptively transferred T cells in vivo," 35(3):276-82 (2012).
Lowe et al., "A novel monoclonal antibody to CD40 prolongs islet allograft survival," Am J Transplant. 12(8):2079-87 (2012).
Luqman et al., "The antileukemia activity of a human anti-CD40 antagonist antibody, HCD122, on human chronic lymphocytic leukemia cells," Blood. 112(3):711-20 (2008).
Molano et al., "Prolonged islet allograft survival in diabetic NOD mice by targeting CD45RB and CD154," Diabetes. 52(4):957-64 (2003).
Najafian et al., "CTLA4-lg: a novel immunosuppressive agent," Expert Opin Investig Drugs. 9(9):2147-57 (2000).
Office Action for Chinese Application No. 201280022277.3, dated Aug. 25, 2014 (19 pages).
Office Action for Japanese Application No. 2013-557941, dated Oct. 27, 2015 (16 pages).
Oura et al., "Long-term hepatic allograft acceptance based on CD40 blockade by ASKP1240 in nonhuman primates," Am J Transplant. 12(7):1740-54 (2012).
Pearson et al., "Anti-CD40 therapy extends renal allograft survival in rhesus macaques," Transplantation. 74(7):933-40 (2002).
Rudikoff et al., "Single amino acid substitution altering antigen-binding specificity," Proc Natl Acad Sci U S A. 79(6):1979-83 (1982).
Russo et al., "Platelet-activating factor mediates CD40-dependent angiogenesis and endothelial-smooth muscle cell interaction," J Immunol. 171(10):5489-97 (2003).
Sho et al., "Requirements for induction and maintenance of peripheral tolerance in stringent allograft models," Proc Natl Acad Sci USA. 102(37):13230-5 (2005).
Strohl, "Optimization of Fc-mediated effector functions of monoclonal antibodies," Curr Opin Biotechnol. 20(6):685-91 (2009).
Sutherland et al., "Anti-CD45RB antibody deters xenograft rejection by modulating T cell priming and homing," Int Immunol. 14(8):953-62 (2002).
Thompson et al., "CD40-specific costimulation blockade enhances neonatal porcine islet survival in nonhuman primates," Am J Transplant. 11(5):947-57 (2011).
Office Action for Japanese Application No. 2013-557941, dated Jul. 26, 2016 (8 pages).
Communication and substantive Office Action for European Patent Application No. 12758099.1, dated Dec. 22, 2016 (7 pages).
Gershoni et al., "Epitope mapping—the first step in developing epitope-based vaccines," BioDrugs. 21(3):145-56 (2007).
Morris, Epitope mapping of protein antigens by competition ELISA. The Protein Protocols Handbook. Humana Press, 595-600 (1996).
Final Rejection for Japanese Application No. 2013-557941, dated Mar. 7, 2017 (10 pages).
Winter et al., "Humanized antibodies," Trends Pharmacol Sci. 14(5):139-43 (1993).
Queen et al.,"A humanized antibody that binds to the interleukin 2 receptor," Proc Natl Acad Sci U.S.A. 86(24):10029-33 (1989).
Kettleborough et al., "Humanization of a mouse monoclonal antibody by CDR-grafting: the importance of framework residues on loop conformation," Protein Eng. 4(7):773-83 (1991).
Carter et al., "Humanization of an anti-p185HER2 antibody for human cancer therapy," Proc Natl Acad Sci U.S.A. 89(10):4285-9 (1992).
Almagro et al., "Humanization of antibodies," Front Biosci. 13:1619-33 (2008).
Roguska et al., "Humanization of murine monoclonal antibodies through variable domain resurfacing," Proc Natl Acad Sci U.S.A. 91(3):969-73 (1994).

* cited by examiner

Description: Mouse anti-CD40 clone 2C10

Heavy chain (signal peptide + V-region)

ATGGAAAGGCACTGGATCTTTCTCTTCCTGTTGTCAGTAACTGCAGGTGTCCAC
TCCCAGGTCCAGCTGCAACAGTCTGGGGCTGAACTGGCAAAACCTGGGGCCT
CAGTGAAGATGTCCTGTAAGGCTTCTGGCTACACCTTTACTAACTACTGGATGC
ACTGGGTAAAACAGAGGCCTGGACAGGGTCTGGAATGGATTGGATACATTAAT
CCTAGCAATGATTATACTAAGTACAATCAAAAGTTCAAGGACAAGGCCACATTG
ACTGCAGACAAATCCTCCAACACAGCCTACATGCAACTGGGTAGCCTGACATCT
GAGGACTCTGCAGTCTATTATTGTGCAAGACAGGGGTTTCCTTACTGGGGCCA
AGGGACTCTGGTCACTGTCTCT

Protein

MERHWIFLFLLSVTAGVHSQVQLQQSGAELAKPGASVKMSCKASGYTFTNYW
MHWVKQRPGQGLEWIGYINPSNDYTKYNQKFKDKATLTADKSSNTAYMQLGSL
TSEDSAVYYCARQGFPYWGQGTLVTVS

Light chain (signal peptide + V-region)

DNA

ATGGATTTTCAAGTGCAGATTTTCAGCTTCCTGCTAATCAGTGCCTCAGTCATAA
TATCCAGAGGACAAATTGTTCTCACCCAGTCTCCAGCAATCATGTCTGCATCTCC
AGGGGAGAAGGTCACCATGACCTGCAGTGCCAGCTCAAGTGTAAGTTACATGC
ACTGGTACCACCAGAGGTCAGGCACCTCCCCCAAAAGATGGATTTATGACACA
TCCAAACTGGCTTCTGGAGTCCCTGCTCGCTTCAGTGGCAGTGGGTCTGGGAC
CTCTTACTCTCTCACAATCAGCAGCATGGAGGCTGAAGATGCTGCCACTTATTAC
TGCCACCAGTTGAGTAGTGACCCATTCACGTTCGGCTCGGGGACAAAGTTGGA
AATAAAA

Protein

MDFQVQIFSFLLISASVIISRGQIVLTQSPAIMSASPGEKVTMTCSASSSVSYMHW
YHQRSGTSPKRWIYDTSKLASGVPARFSGSGSGTSYSLTISSMEAEDAATYYCHQL
SSDPFTFGSGTKLEIK

Figure 1

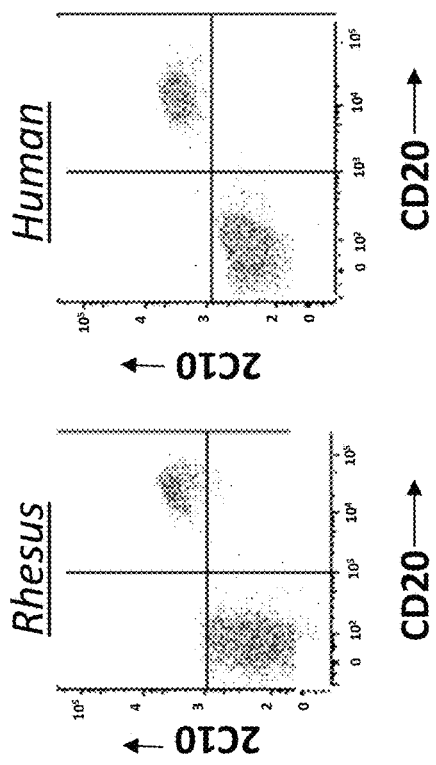
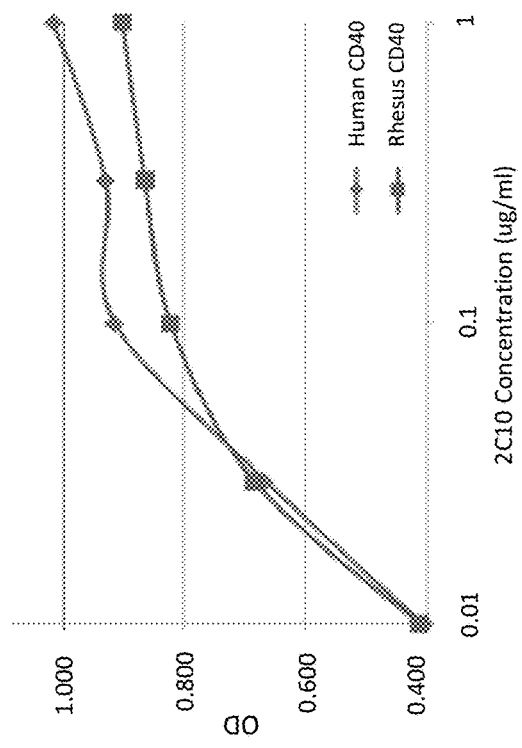
FIG. 2A
FIG. 2B
Figures 2A-2B

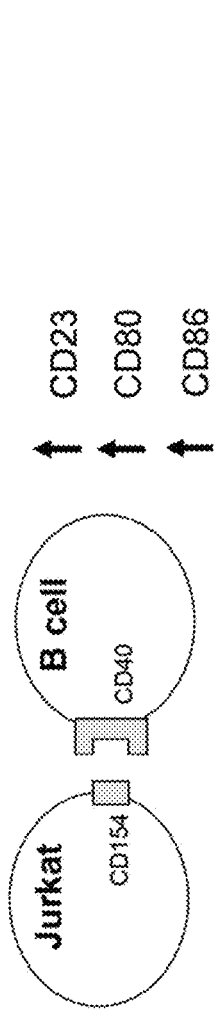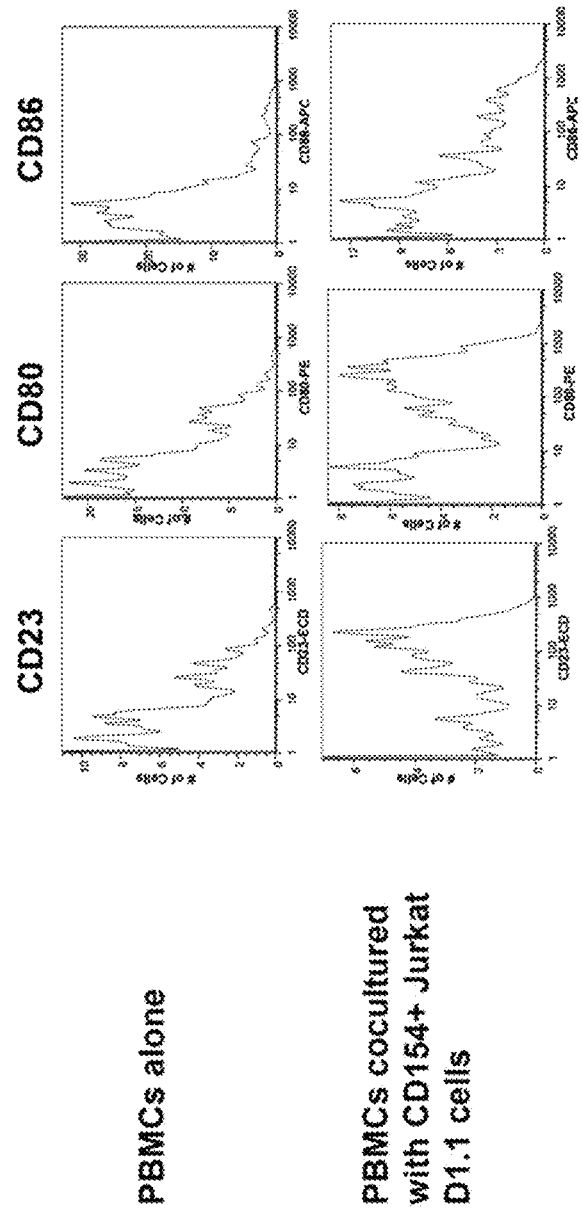
Figure 4

SEQUENCE LISTING

<160> NUMBER OF SEQ ID NOS: 10

<210> SEQ ID NO 1
<211> LENGTH: 396
<212> TYPE: DNA
<213> ORGANISM: Artificial Sequence
<220> FEATURE:
<223> OTHER INFORMATION: Synthetic Construct

<400> SEQUENCE: 1

```
atggaaaggc actggatctt tctcttcctg ttgtcagtaa ctgcaggtgt ccactcccag    60
gtccagctgc aacagtctgg ggctgaactg gcaaaacctg gggcctcagt gaagatgtcc   120
tgtaaggctt ctggctacac ctttactaac tactggatgc actgggtaaa acagaggcct   180
ggacagggtc tggaatggat tggatacatt aatcctagca atgattatac taagtacaat   240
caaaagttca aggacaaggc cacattgact gcagacaaat cctccaacac agcctacatg   300
caactgggta gcctgacatc tgaggactct gcagtctatt attgtgcaag acaggggttt   360
ccttactggg gccaagggac tctggtcact gtctct                             396
```

<210> SEQ ID NO 2
<211> LENGTH: 132
<212> TYPE: PRT
<213> ORGANISM: Artificial Sequence
<220> FEATURE:
<223> OTHER INFORMATION: Synthetic Construct

<400> SEQUENCE: 2

```
Met Glu Arg His Trp Ile Phe Leu Phe Leu Leu Ser Val Thr Ala Gly
1               5                   10                  15

Val His Ser Gln Val Gln Leu Gln Gln Ser Gly Ala Glu Leu Ala Lys
            20                  25                  30

Pro Gly Ala Ser Val Lys Met Ser Cys Lys Ala Ser Gly Tyr Thr Phe
        35                  40                  45

Thr Asn Tyr Trp Met His Trp Val Lys Gln Arg Pro Gly Gln Gly Leu
    50                  55                  60

Glu Trp Ile Gly Tyr Ile Asn Pro Ser Asn Asp Tyr Thr Lys Tyr Asn
65                  70                  75                  80

Gln Lys Phe Lys Asp Lys Ala Thr Leu Thr Ala Asp Lys Ser Ser Asn
                85                  90                  95

Thr Ala Tyr Met Gln Leu Gly Ser Leu Thr Ser Glu Asp Ser Ala Val
            100                 105                 110

Tyr Tyr Cys Ala Arg Gln Gly Phe Pro Tyr Trp Gly Gln Gly Thr Leu
        115                 120                 125

Val Thr Val Ser
    130
```

<210> SEQ ID NO 3
<211> LENGTH: 384
<212> TYPE: DNA
<213> ORGANISM: Artificial Sequence
<220> FEATURE:
<223> OTHER INFORMATION: Synthetic Construct

<400> SEQUENCE: 3

```
atggattttc aagtgcagat tttcagcttc ctgctaatca gtgcctcagt cataatatcc    60
agaggacaaa ttgttctcac ccagtctcca gcaatcatgt ctgcatctcc aggggagaag   120
gtcaccatga cctgcagtgc cagctcaagt gtaagttaca tgcactggta ccaccagagg   180
tcaggcacct cccccaaaag atggatttat gacacatcca actggcttc tggagtccct   240
gctcgcttca gtggcagtgg gtctgggacc tcttactctc tcacaatcag cagcatggag   300
gctgaagatg ctgccactta ttactgccac cagttgagta gtgacccatt cacgttcggc   360
tcggggacaa agttggaaat aaaa                                          384
```

-continued

```
<210> SEQ ID NO 4
<211> LENGTH: 128
<212> TYPE: PRT
<213> ORGANISM: Artificial Sequence
<220> FEATURE:
<223> OTHER INFORMATION: Synthetic Construct

<400> SEQUENCE: 4

Met Asp Phe Gln Val Gln Ile Phe Ser Phe Leu Leu Ile Ser Ala Ser
1               5                   10                  15

Val Ile Ile Ser Arg Gly Gln Ile Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Val Ser Tyr Met His Trp Tyr His Gln Arg Ser Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys His Gln Leu
            100                 105                 110

Ser Ser Asp Pro Phe Thr Phe Gly Ser Gly Thr Lys Leu Glu Ile Lys
        115                 120                 125

<210> SEQ ID NO 5
<211> LENGTH: 100
<212> TYPE: PRT
<213> ORGANISM: Artificial Sequence
<220> FEATURE:
<223> OTHER INFORMATION: Synthetic Construct

<400> SEQUENCE: 5

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Ser Glu Ser Glu Phe Leu
        35                  40                  45

Asp Thr Trp Asn Arg Glu Thr Arg Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Leu His Cys Met Ser Glu Ser Cys
                85                  90                  95

Glu Ser Cys Val
            100

<210> SEQ ID NO 6
<211> LENGTH: 100
<212> TYPE: PRT
<213> ORGANISM: Artificial Sequence
<220> FEATURE:
<223> OTHER INFORMATION: Synthetic Construct

<400> SEQUENCE: 6

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30
```

```
Glu Phe Thr Glu Thr Glu Cys Leu Pro Cys Gly Glu Ser Glu Phe Leu
            35                  40                  45

Asp Thr Trp Asn Arg Glu Thr His Cys His Gln His Lys Tyr Cys Asp
 50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
                85                  90                  95

Glu Ser Cys Val
            100

<210> SEQ ID NO 7
<211> LENGTH: 30
<212> TYPE: DNA
<213> ORGANISM: Artificial Sequence
<220> FEATURE:
<223> OTHER INFORMATION: Synthetic Construct

<400> SEQUENCE: 7
ctaacactca ttcctgttga agctcttgac                                         30

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
gctgatgctg caccaactgt atcc                                               24

<210> SEQ ID NO 9
<211> LENGTH: 20
<212> TYPE: DNA
<213> ORGANISM: Artificial Sequence
<220> FEATURE:
<223> OTHER INFORMATION: GGC AAC GTT GCA GGT CTC GC

<400> SEQUENCE: 9
ggcaacgttg caggtctcgc                                                    20

<210> SEQ ID NO 10
<211> LENGTH: 26
<212> TYPE: DNA
<213> ORGANISM: Artificial Sequence
<220> FEATURE:
<223> OTHER INFORMATION: Synthetic Construct

<400> SEQUENCE: 10
ctggatctgc tgcccaaact aactcc                                             26
```

POLYNUCLEOTIDES ENCODING ANTI-CD40 ANTIBODIES

STATEMENT AS TO FEDERALLY FUNDED RESEARCH

This invention was made with government support under Grant HHSN272200900037C awarded by NIH. The Government has certain rights in the invention.

BACKGROUND OF THE INVENTION

The invention relates to anti-CD40 antibodies and uses of such antibodies, for example, to reduce the likelihood of, or increase the duration prior to, transplant rejection, to induce immunosuppression, or to treat an autoimmune disorder.

Suppression of the immune system, particularly the humoral immune system, is beneficial in organ transplantation and treatment of autoimmune disorders. Organ transplantation, for example, has emerged as a preferred method of treatment for many forms of life-threatening diseases that involve organ damage. Transplantation rejection occurs when an organism receiving transplanted cells or tissue mounts an undesired immune response to that tissue. Transplant rejection can be minimized by tissue-type matching, but even matched tissue is generally rejected by the donor. Thus, immunosuppressive therapies are required for virtually all cases of tissue transplantation.

Improved results in clinical transplantation have been achieved primarily through the development of increasingly potent non-specific immunosuppressive drugs to inhibit rejection responses. While short-term results have improved, long-term outcomes remain inadequate. Life-long immunosuppressive agents may be required to combat chronic rejection of the transplanted organ, and the use of these agents dramatically increases the risks of cardiovascular disease, infections, and malignancies.

One potential target for reducing transplantation rejection is the CD40/CD154 interaction. CD40 is expressed on the surface B lymphocytes and CD154 is expressed on surface of T cells. The interaction between these two proteins is associated with B cell activation, which triggers cytokine expression as well as expression of cell surface markers including CD23, CD80, and CD86. Blockade of this interaction using anti-CD154 antibodies has been shown to reduce or eliminate rejection of transplanted tissues in non-human primates.

For any type of immunosuppression (e.g., in a transplantation procedure), a balance between efficacy and toxicity is a key factor for its clinical acceptance. Thus, there is a need for therapies that specifically target the immunological pathways involved in, for example, transplant rejection and autoimmune disorders.

SUMMARY OF THE INVENTION

In a first aspect, the invention features an isolated antibody, or antigen-binding fragment thereof (e.g., an antibody that lacks an Fe portion or is a F(ab')$_2$, a Fab, an Fv, or an scFv structure), that specifically binds to an epitope present on CD40 (e.g., rhesus, murine, or human CD40), where the epitope is recognized by the 2C10 antibody (e.g., where said epitope is not recognized by the 3A8 or the Chi220 antibody, or both). The antibody may be capable of blocking B lymphocyte (e.g., rhesus or human B lymphocyte) activation by CD154-expressing Jurkat cells in vitro or may be capable of inhibiting rhesus B cells in vitro, e.g., reducing CD23, CD80, or CD86 expression. The antibody may be the 2C10 antibody. The antibody may have human constant regions. In certain embodiments, the antibody is a humanized antibody or a human antibody. In certain embodiments, the antibody may be monoclonal antibody or a polyclonal antibody.

In particular embodiments, the antibody includes the heavy chain variable region defined by amino acids 20-132 of SEQ ID NO:2, an antibody-binding portion or fragment thereof, or a humanized form thereof. In other embodiments, the antibody light chain variable region of the antibody includes the sequence of 23-128 of SEQ ID NO:4, an antibody binding portion or fragment thereof, or a humanized form thereof. In other embodiments, the heavy chain variable region of the antibody includes amino acids 20-132 of SEQ ID NO:2 and the light chain variable sequence of the antibody includes amino acids 23-128 of SEQ ID NO:4.

The invention also features a polynucleotide encoding the antibody or antibody fragment of the first aspect, a vector including the polynucleotide, and a cell including the vector. The cell may be eukaryotic (e.g., mammalian such a human, mouse, monkey or rabbit cell) or may be prokaryotic (e.g., a bacterial cell such as an *E. coli* cell).

In another aspect, the invention features a method of suppressing the immune system in a subject (e.g., a mammal such as human). The method includes administering to the subject an effective amount of an antibody, or antigen-binding fragment thereof, of the first aspect to the subject.

In yet another aspect, the invention features a method of treating or treating prophylactically transplant rejection or increasing the duration of time before transplant rejection occurs in a subject (e.g., a mammal such as a human) in need thereof. The method includes administering an effective amount of an antibody, or antigen-binding fragment thereof, of the first aspect to the subject.

In either of the previous two aspects, the subject may have received, or may be in need of, an organ transplant (e.g., a heart, kidney, lung, liver, pancreas, intestine, and thymus, or a portion thereof) or a tissue transplant (e.g., bone, tendon, cornea, skin, heart valve, vein, or bone marrow).

In any of the previous two aspects, administration may be commenced prior to the transplantation or the graft. Administration may continue for at least 1, 2, 3, 4, 5, 7 or 10 days; 2, 3, 4, 6, 8, 10, or 12 weeks; 3, 4, 5, 6, 8, 10, 12, 24, or 36 months following the transplantation or the graft.

In yet another aspect, the invention features a method of treating or treating prophylactically graft-versus-host disease in a subject (e.g., a mammal such as a human) in need thereof. The method includes administering an effective amount of an antibody, or an antigen-binding fragment thereof, of the first aspect to the subject.

In another aspect, the invention features a method of treating or treating prophylactically an autoimmune disorder in a subject (e.g., a mammal such as a human) in need thereof. The method includes administering an effective amount of an antibody, or an antigen-binding fragment thereof, of the first aspect to the subject. In certain embodiments, the autoimmune disorder is associated with or caused by the presence of an autoantibody (e.g., systemic lupus erythematosus (SLE), CREST syndrome (calcinosis, Raynaud's syndrome, esophageal dysmotility, sclerodactyl, and telangiectasia), opsoclonus, inflammatory myopathy (e.g., polymyositis, dermatomyositis, and inclusion-body myositis), systemic scleroderma, primary biliary cirrhosis, celiac disease (e.g., gluten sensitive enteropathy), dermatitis herpetiformis, Miller-Fisher Syndrome, acute motor axonal neuropathy (AMAN), multifocal motor neuropathy with conduction block, autoimmune hepatitis, antiphospholipid syndrome, Wegener's granulomatosis, microscopic polyangiitis, Churg-Strauss syndrome, rheumatoid arthritis, chronic autoimmune hepatitis, scleromyositis, myasthenia gravis, Lambert-Eaton myasthenic syndrome, Hashimoto's thyroiditis, Graves' disease, Paraneoplastic cerebellar degeneration, Stiff person syndrome, limbic encephalitis, Isaacs Syndrome, Sydenham's chorea, pediatric autoimmune neuropsychiatric disease associated with *Streptococcus* (PANDAS), encephalitis, diabetes mellitus type 1, and Neuromyelitis optica). In other embodiments, the disorder is selected from the group consisting of pernicious anemia, Addison's disease, psoriasis, inflammatory bowel disease, psoriatic arthritis, Sjögren's syndrome, lupus erythematosus (e.g., discoid lupus erythematosus, drug-induced lupus erythematosus, and neonatal lupus erythematosus), multiple sclerosis, and reactive arthritis. In still other embodiments, the disorder is selected from the group consisting of polymyositis, dermatomyositis, multiple endocrine failure, Schmidt's syndrome, autoimmune uveitis, adrenalitis, thyroiditis, autoimmune thyroid disease, gastric atrophy, chronic hepatitis, lupoid hepatitis, atherosclerosis, prescnile dementia, demyelinating diseases, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, alopecia arcata, pemphigoid, scleroderma, progressive systemic sclerosis, adult onset diabetes mellitus (e.g., type II diabetes), male and female autoimmune infertility, ankylosing spondolytis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic cncephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, endocarditis, endomyocardial fibrosis, endophthalmitis, erythema elevatum et diutinum, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, mumps, Evan's syndrome, and autoimmune gonadal failure.

In any of the previous three aspects, administration may be parenteral, intravenous, subcutaneous, oral, topical, intrathecal, local, or by any route described herein.

In any of the previous four aspects, the method may further include administration of second agent within six months (e.g., within 3, 2, or 1 months; within 4, 3, 2, or 1 weeks; within 6, 5, 4, 3, 2, or 1 days; or within 18, 12, 6, 3, 2, or 1 hours of antibody administration), where the second agent is an immunosuppressant. The second agent may be selected from the group consisting of a calcineurin inhibitor (e.g., cyclosporin A or cyclosporine G), tacrolimus, an mTor inhibitor (e.g., sirolimus, temsirolimus, zotarolimus, or everolimus), fingolimod, myriocin, alemtuzumab, rituximab, an anti-CD4 monoclonal antibody, an anti-LFA1 monoclonal antibody, an anti-LFA3 monoclonal antibody, an anti-CD45 antibody (e.g., an anti-CD45RB antibody), an anti-CD19 antibody, monabatacept, belatacept, indolyl-ASC; azathioprine, lymphocyte immune globulin and anti-thymocyte globulin [equine], mycophenolate mofetil, mycophenolate sodium, daclizumab, basiliximab, cyclophosphamide, prednisone, prednisolone, leflunomide, FK778, FK779, 15-deoxyspergualin, busulfan, fludarabine, methotrexate, 6-mercaptopurine, 15-deoxyspergualin, LF15-0195, bredinin, brequinar, and muromonab-CD3. In certain embodiments, the second agent is belatacept.

In still another aspect, the invention features a method of making an antibody. The method includes: (a) administering to a mammal (e.g., a mouse or a rabbit) a polypeptide that comprises a fragment (e.g., less than 50, 40, 30, 20, 10 amino acids in length, but more than 6, 8, or 10 amino acids in length) of the CD40 polypeptide that includes the epitope recognized by the 2C10 antibody, but not the full length CD40 molecule in a manner sufficient to generate an immune response to said fragment; (b) isolating spleen cells from the mammal; (c) forming a hybridoma between the spleen cells and myeloma cells; and (d) purifying the antibody produced by the hybridoma. The polypeptide may be a fusion protein (e.g., between the CD40 fragment and keyhole limpet hemocyanin or glutathione S-transferase). The invention also features an antibody produced by such a method.

In another aspect, the invention features a fragment of CD40 fewer than 150 (e.g., fewer than 120, 100, 80, 70, 60, 50, 40, 30, 20, 15, 12, 11, 10, 9, 8, or 7) amino acids in length that is specifically bound by the 2C11 antibody. In certain embodiments, the fragment is 8-10, 8-12, 8-15, 8-20, 8-30, 8-40, 8-50, 8-60, 8-70, 8-80, or 8-100 amino acids in length. In other embodiments, the fragment is 7-10, 7-12, 7-15, 7-20, 7-30, 7-40, 7-50, 7-60, 7-70, 7-80, or 7-100 in length. The CD40 fragment may be from the extracellular domain of CD40 (e.g., SEQ ID NOS:5 and 6). The invention also features a fusion protein including a fragment described herein and a heterologous sequence.

By "specifically binds" is meant a compound or antibody that recognizes and binds a particular epitope but does not substantially recognize and bind other molecules present in a sample (e.g., a biological sample which naturally includes other polypeptides, nucleic acids, and/or other biological molecules). In one example, an antibody that specifically binds the CD40 epitope recognized by the 2C10 antibody does not bind other epitopes present on CD40.

By "antigen-binding fragment" of an antibody is meant any fragment or portion of an antibody that has the ability to specifically bind the target antigen of the full length antibody.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) of the recipient are replaced by residues from a HVR of a non-human species (donor antibody) such as mouse, rat, rabbit, or nonhuman primate having the desired specificity, affinity, and/or capacity. In some instances, framework (FR) residues (i.e., residues in the variable regions other than the hypervariable regions) of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody can comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., Nature 321:522-25, 1986; Riechmann et al., Nature 332:323-29, 1988; and Presta, Curr. Op. Struct. Biol. 2:593-6, 1992. See also, e.g., Vaswani et al., Ann. Allergy Asthma & Immunol. 1:105-15, 1998; Harris, Biochem. Soc. Transactions 23:1035-8, 1995; Hurle et al., Curr. Op. Biotech. 5:428-33, 1994; and U.S. Pat. Nos. 6,982,321 and 7,087,409.

A "human antibody" is one that possesses an amino acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries (Hoogenboom et al., J. Mol. Biol 227:381-8, 1992; Marks et al., J. Mol. Biol, 222:581-97, 1991). Also available for the preparation of human monoclonal antibodies are methods described in Cole et al., Monoclonal Antibodies and Cancer Therapy, Alan R. Liss, p. 77 (1985); Boemer et al., J. Immunol. 147:86-95, 1991. See also van Dijk et al., Curr. Opin. Pharmacol. 5:368-74, 2001. Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XenoMouse® technology). See also, for example, Li et al., Proc. Natl. Acad. Sci. USA 103:3557-62, 2006 regarding human antibodies generated via a human B-cell hybridoma technology.

By "treating" a disease, disorder, or condition in a subject is meant reducing at least one symptom of the disease, disorder, or condition by administrating a therapeutic agent to the subject.

By "treating prophylactically" a disease, disorder, or condition in a subject is meant reducing the frequency of occurrence or severity of (e.g., preventing) a disease, disorder or condition by administering to the subject a therapeutic agent to the subject prior to the appearance of a disease symptom or symptoms.

The term "an effective amount" means the dose needed to effectively treat the physiological effects of a medical condition (e.g., transplant rejection or graft-versus-host disease).

By "immunosuppressant" is meant a compound or composition that induces immunosuppression, i.e., it reduces (e.g., prevents) or interferes with the development of an immunologic response (e.g., cellular or humoral).

By "subject" is meant a human or non-human animal (e.g., a mammal).

By "fusion protein" is meant a polypeptide that contains (a) a protein or fragment thereof of interest; and (b) a heterologous fusion partner.

Other features and advantages of the invention will be apparent from the following Detailed Description, the drawings, and the claims.

BRIEF DESCRIPTION OF THE DRAWINGS

FIG. 1 shows the variable regions from the heavy chain and the light chain of the 2C10 antibody. The nucleotide sequence shown for the heavy chain (SEQ ID NO: 1) includes a signal peptide (nucleotides 1-57; underlined) and the heavy chain variable sequence (nucleotides 58-396). The corresponding amino acid sequence is shown below (SEQ ID NO:2), where amino acids 1-19 corresponding to the signal sequence (underlined) and amino acids 20-132 correspond to the heavy chain variable region.

The nucleotide sequence shown for the light chain (SEQ ID NO:3) includes a signal peptide (nucleotides 1-66; underlined) and the light chain variable sequence (nucleotides 67-384). The corresponding amino acid sequence is shown below (SEQ ID NO:4), where amino acids 1-22 correspond to the signal peptide (underlined) and amino acids 23-128 correspond to the light chain variable region.

FIG. 2A is a plot showing flow cytometry data confirming the binding of 2C10 to human and rhesus CD20+ B cells.

FIG. 2B is a plot showing CD40 adsorption data from ELISA assays with varying concentrations of 2C10 to confirm the binding of 2C10 to human and rhesus CD40 as detected using goat anti-mouse IgG-HRP.

Figure 3:
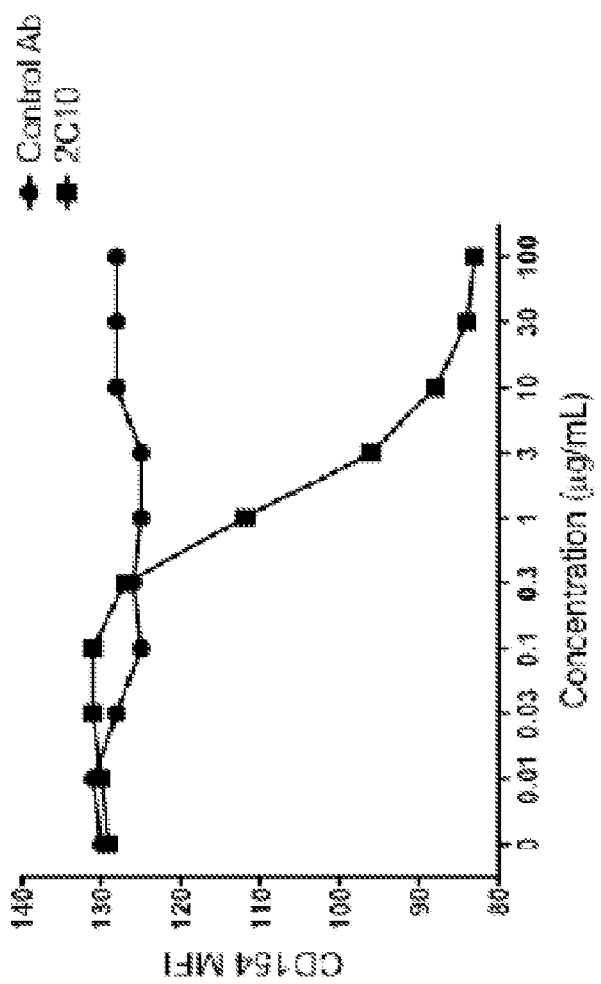

FIG. 3 is a graph showing the dose-dependent inhibition of CD154 binding to B cells by 2C10. B cells were analyzed for CD154 binding by incubating with histidine-tagged soluble CD154 and analyzing for histidine expression. Results are representative of multiple repetitions of the experiment.

FIG. 4 is a schematic diagram and graphs showing the principle of the assay involving rhesus or human peripheral blood mononuclear cells (PBMCs) and Jurkat cells.

Figure 5:
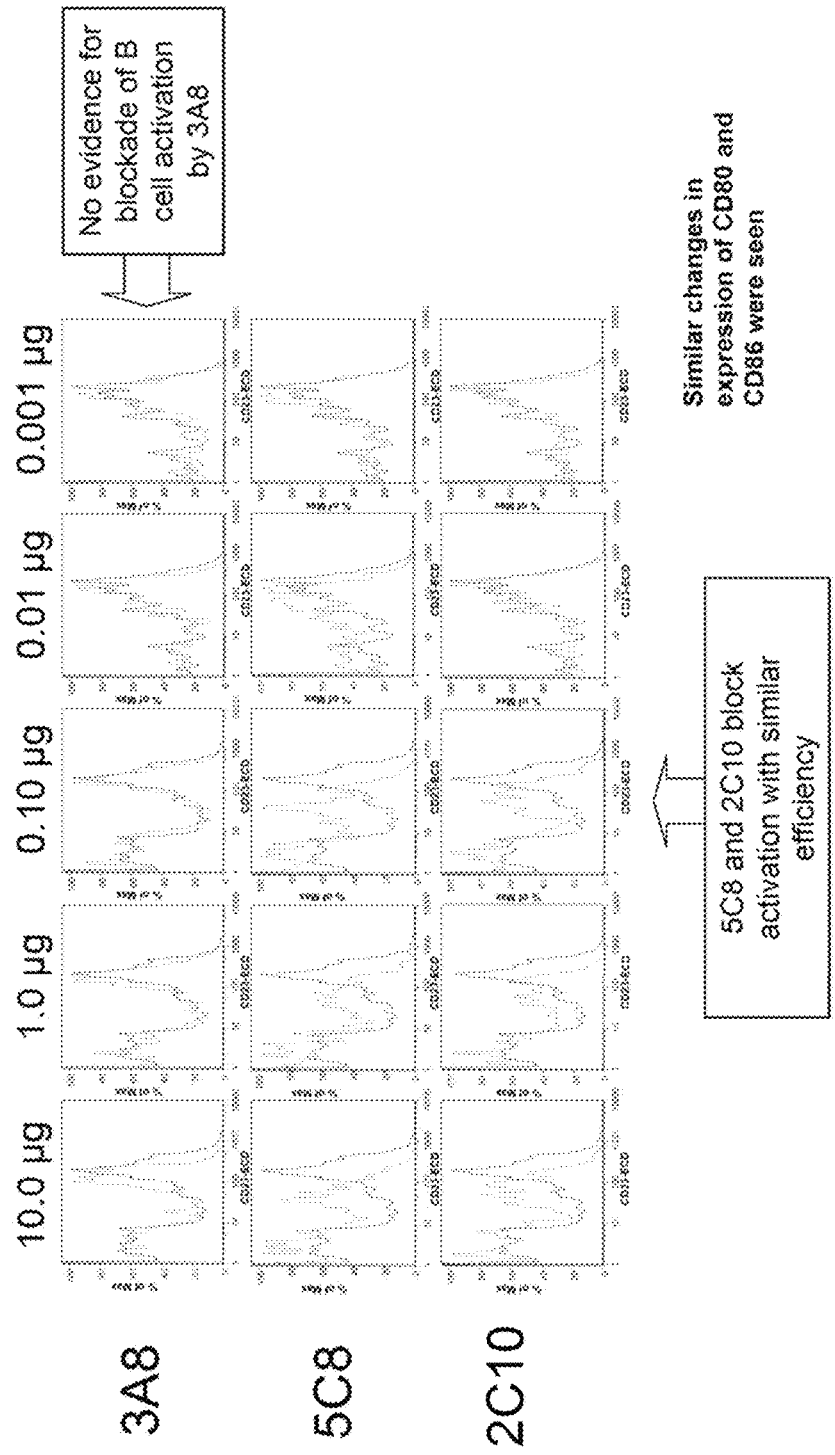

FIG. 5 is a set of graphs showing CD23 expression in CD20+ cells taken from co-cultures of rhesus PBMCs and Jurkat cells in the presence of variable concentrations of 3A8, 5C8, or 2C10 antibodies.

Figure 6:
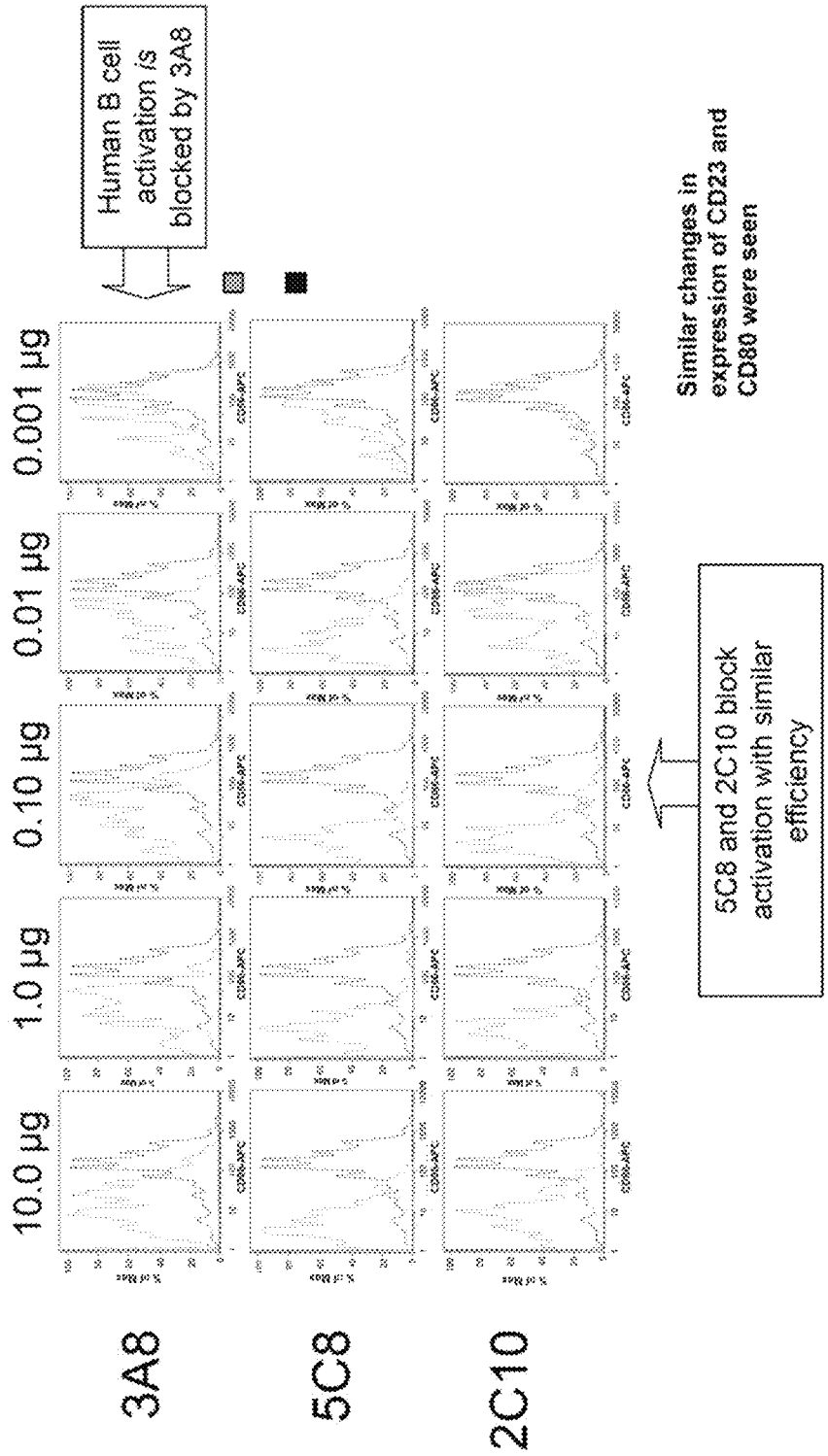

FIG. 6 is a set of graphs showing CD86 expression in CD20+ cells taken from co-cultures of human PBMCs and Jurkat cells in the presence of variable concentrations of 3A8, 5C8, or 2C10 antibodies.

Figure 7:
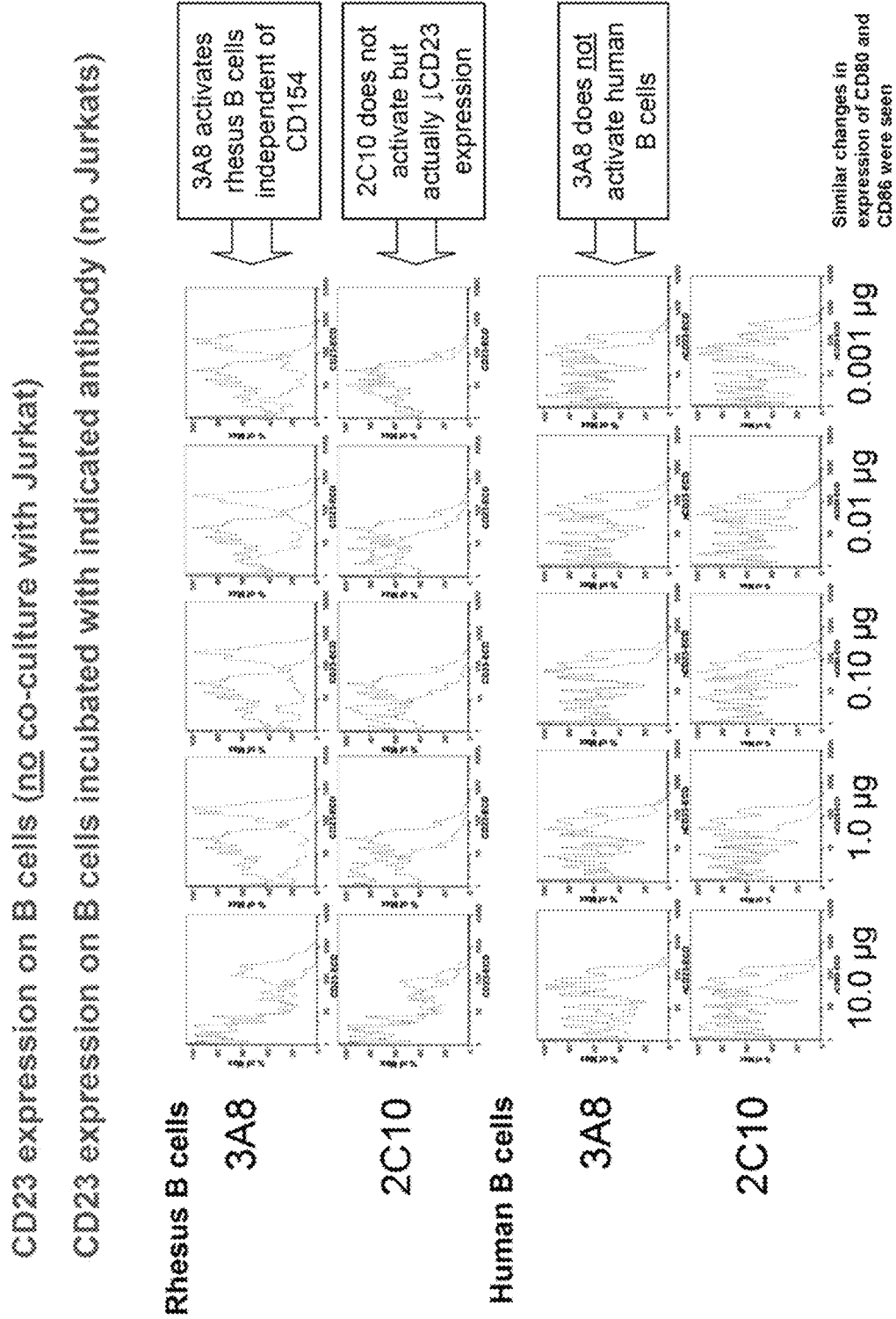

FIG. 7 is a set of graphs showing CD23 expression CD20+ cells from either human or rhesus PBMCs cultured without Jurkat cells in the presence of either the 3A8 or the 2C10 antibody.

Figure 8:
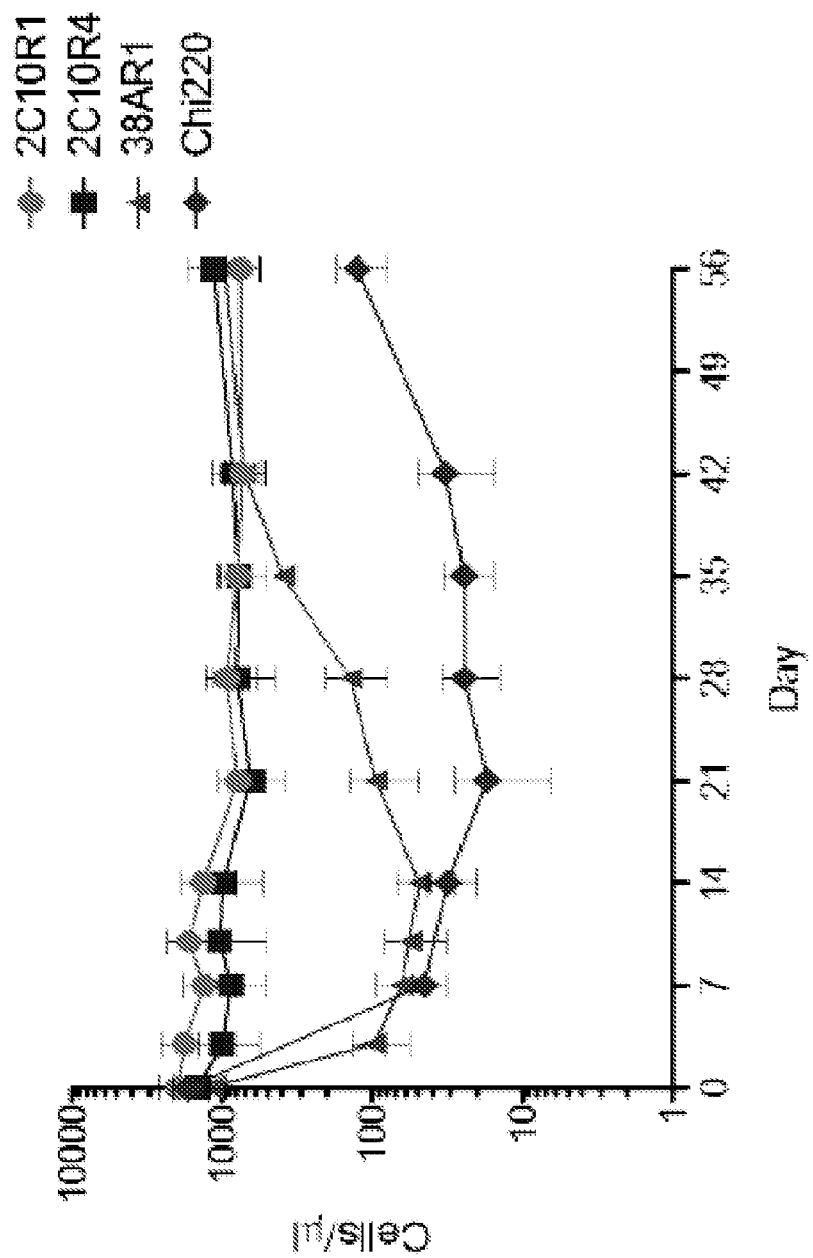

FIG. 8 is a graph showing peripheral B cell count of rhesus macaques treated with mouse-rhesus chimeric forms of 2C10 engineered to contain either rhesus IgG1 (2C10R1) or IgG4 (2C10R4) heavy chain constant regions, and chimeric IgG1 forms of anti-CD40 3A8 (3A8R1) or anti-CD40 Chi220 (Chi220). All animals were immunized with 4-hydroxy-3-nitrophenylacetyl-conjugated keyhole limpet hemocyanin (KLH) after the first antibody treatment.

Figure 9:
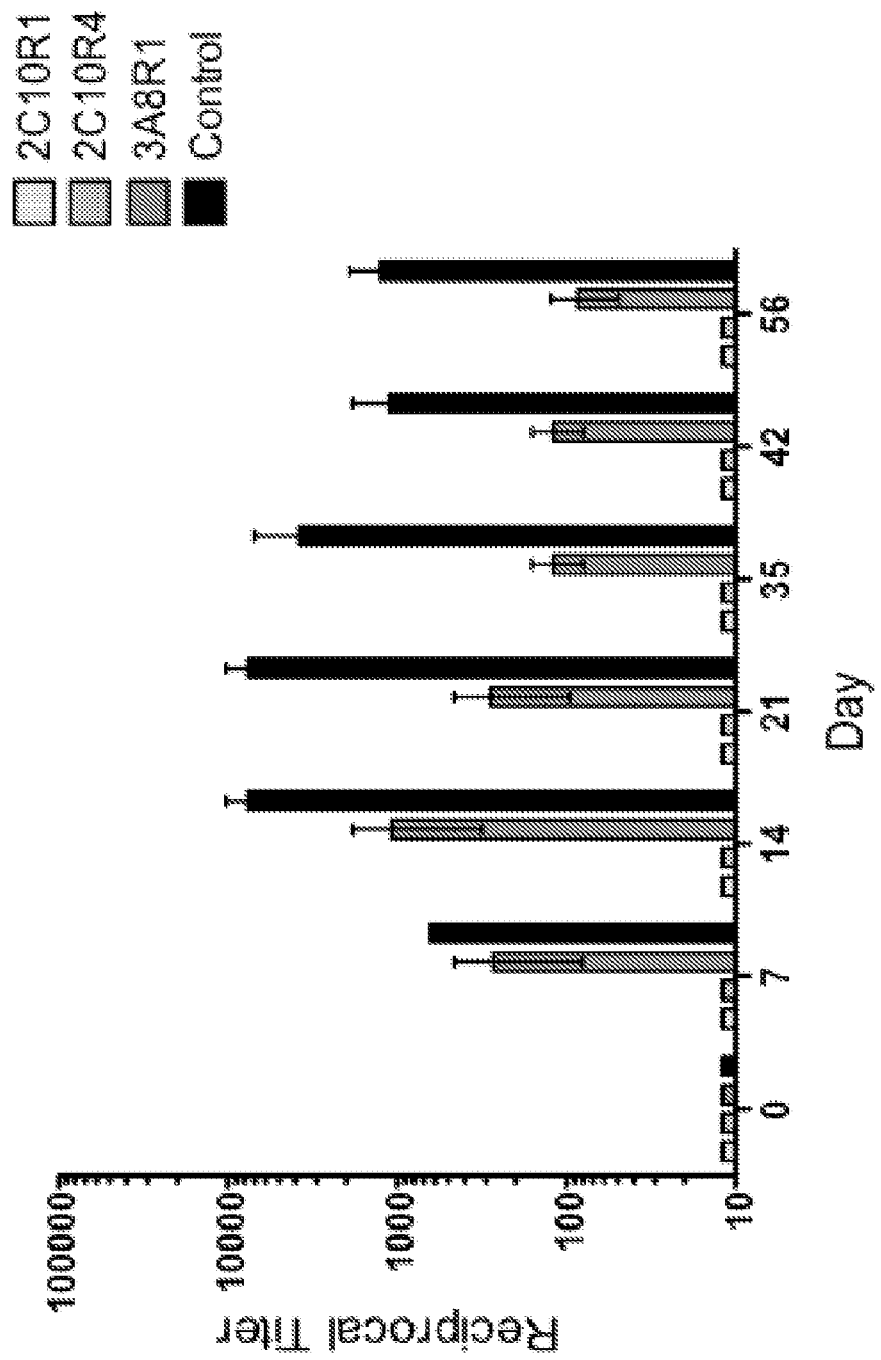

FIG. 9 is a graph showing T cell-dependent antibody responses in macaque monkeys treated with 2C10R1, 2C10R4, or 3A8R1 antibody. All animals were immunized with KLH after the first antibody treatment.

Figure 10:
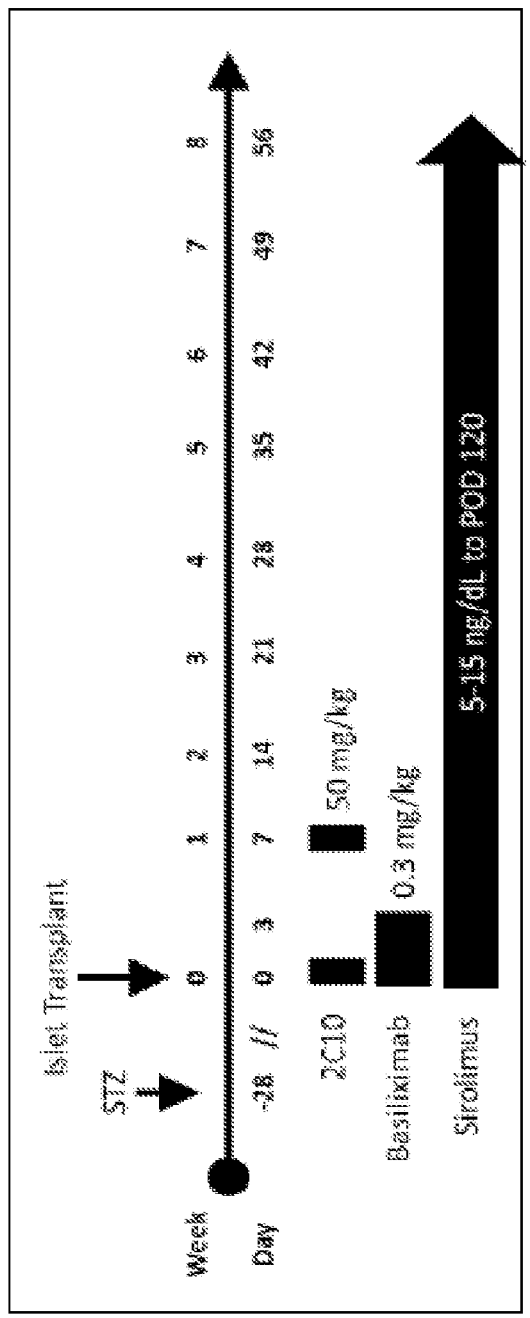

FIG. 10 is a diagram showing the standard macaque model of allogeneic islet transplantation. Diabetes was induced in macaque monkeys using streptozotocin. Diabetic monkeys were transplanted with allogeneic islets and immunosuppresion initiated with basiliximab and sirolumus. Experimental animals received 2C10R4 treatment on days 0 and 7 post-transplantation.

Figures 11A, 11B:
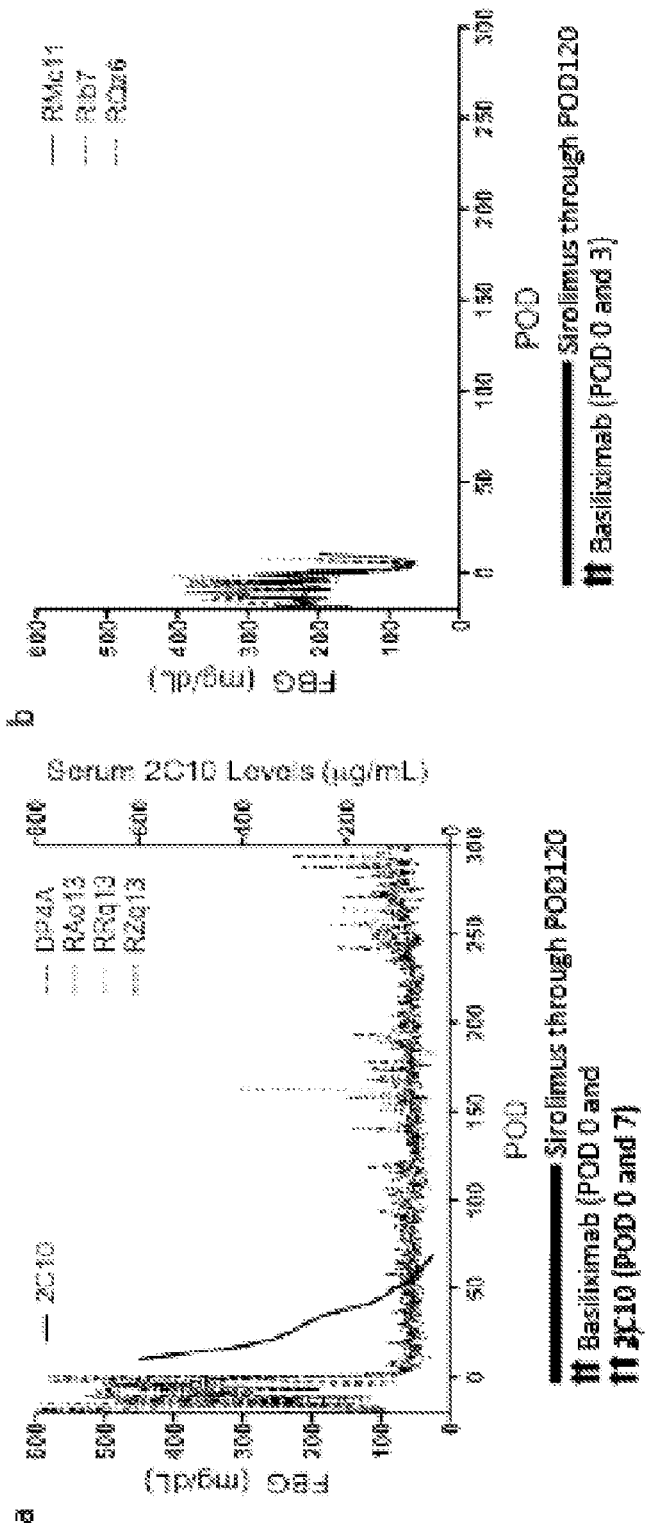

FIG. 11A is a plot showing free blood glucose levels (FBG) in 4 macaques following islet transplantation, background immunosuppresion, and treatment with 2C10R4. The solid line on the plot represents the level of 2C10 in the plasma.

FIG. 11B is a plot showing FBG in macaques that received only background immunosuppresion.

Figure 12:
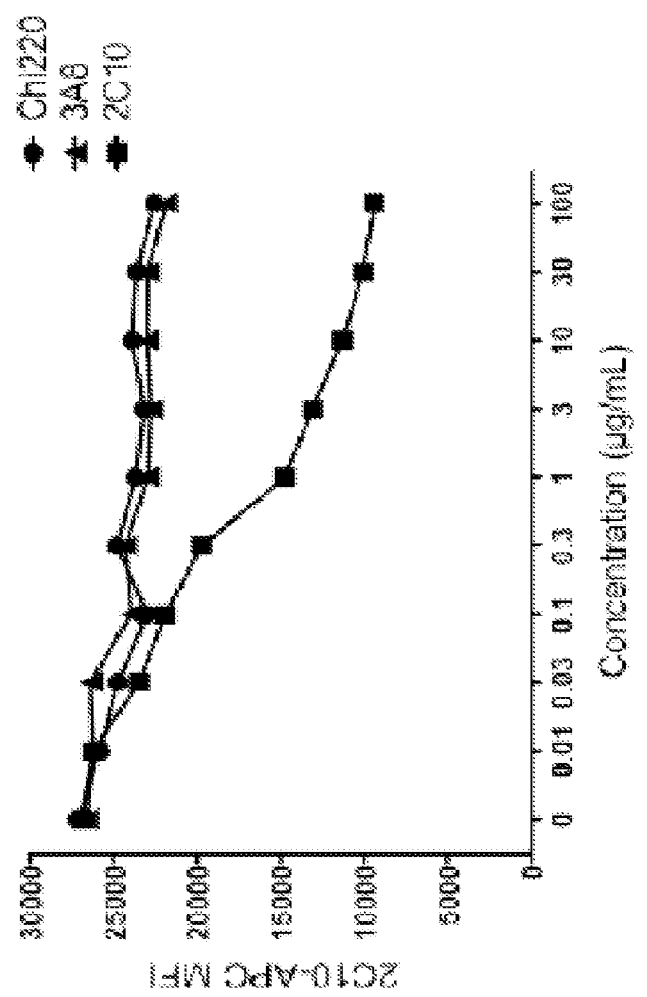

FIG. 12 is a graph showing results from a competitive blockade assay using human PBMCs incubated with increasing concentrations of 2C10, 3A8, or Chi220 antibodies and stained with an APC-conjugated 2C10 to assess the ability of each antibody to cross-block 2C10.

DETAILED DESCRIPTION

The present invention relates to anti-CD40 antibodies and antibody fragments having the ability to bind a particular epitope on the CD40 molecule, as well as methods that involve the use of such antibodies. This epitopic specificity confers a particular activity profile, such that the antibodies generally block the ability of CD40 to interact with its binding partners (e.g., CD154) and do so without activating the cell expressing CD40. This activity profile is understood to make these antibodies particularly useful for reducing complications associated with organ or tissue transplantation.

Production and Identification of CD40 Antibodies

Mice (strain AJ) were immunized with a fusion protein consisting of the extracellular domain of rhesus macaque (*M. mulatta*) CD40 (amino acid sequence: EPPTACREKQYLINSQCCSLCQPGQKLVSDCTEFTETECLPCSESEFLDTWNRETRCHQHKYCDP NLGLRVQQKGTSETDTICTCEEGLHCMSESCESCV; SEQ ID NO:5) fused to maltose binding protein (CD40-MBP). The amino acid sequence in this region of the rhesus macaque CD40 protein differs from human CD40 protein at five amino acid positions (human amino acid sequence: EPPTACREKQYLINSQCCSLCQPGQKLVSDCTEFTETECLPCGESEFLDTWNRETHCHQHKYCDP NLGLRVQQKGTSETDTICTCEEGWHCTSEACESCV; SEQ ID NO:6). CD40-MBP was administered to mice multiple times with complete Freund's adjuvant and incomplete Freund's adjuvant. Splenocytes from immunized mice were fused with the mouse myeloma cell line SP2/0 and hybrids selected using standard hybridoma technology.

Antibodies were selected for reactivity to a second fusion protein consisting of the same rhesus CD40 domain fused to glutamine synthetase (CD40-GST). Antibodies reactive to CD40-GST by ELISA were further tested for reactivity to native CD40 express on rhesus macaque blood B cells, human blood B cells and rhesus macaque B-lymphoblastoid cell lines by flow cytometry. As a final level of selection, antibodies were tested in an in vitro assay for their ability to inhibit human or rhesus macaque B cell activation after co-culture CD154-expressing Jurkat D1.1 cells. A stable subclone of anti-CD40 antibody 2C10 was obtained by limiting dilution. The antibody is a mouse IgG1-kappa.

Antibody Cloning

Variable regions of monoclonal antibodies can be cloned using any method known in the art. PCR-based methods for obtaining antibody variable region sequences for hybridoma cells are described, for example, in Larrick et al., *Nat. Biotechnol.* 7:934-8, 1989 and in Orlandi et al., *Proc. Natl. Acad. Sci. USA* 86:3833-7, 1989. Using these techniques or similar techniques, the variable regions of monoclonal antibodies can be cloned and subject to further manipulation.

In the present case, the variable sequences from the heavy and light chains of the 2C10 antibody were cloned and were sequenced. The DNA representing the immunoglobulin heavy and light chain variable regions from the 2C10 hybridoma were cloned using 5' RACE PCR employing the following DNA primers:

```
Mouse kappa reverse:
                                      (SEQ ID NO: 7)
5'-CTA ACA CTC ATT CCT GTT GAA GCT CTTGAC;

Mouse kappa forward:
                                      (SEQ ID NO: 8)
5'-GCT GAT GCT GCA CCA ACT GTA TCC-3'

Mouse IgG1 reverse:
                                      (SEQ ID NO: 9)
5'-GGC AAC GTT GCA GGT CTC GC-3'

Mouse IgG1 forward:
                                     (SEQ ID NO: 10)
5'-CTG GAT CTG CTG CCC AAA CTA ACT CC-3'
```

PCR products were cloned into a commercial cloning vector and were sequenced using standard sequencing techniques. The resulting sequences are provided in FIG. 1.

The immunoglobulin variable region genes were cloned from the hybridomas secreting anti-CD40 antibody clone 2C10 and from anti-human CD40 clone 3A8 (Kwekkeboom et al., *Immunology* 79:439-44, 1993) (obtained from the American Type Culture Collection, ATCC, Vienna, Va.) using 5' rapid amplification of cDNA ends-polymerase chain reaction. The immunoglobulin heavy and light chain variable regions were subcloned into expression vectors containing rhesus IgG1 or rhesus IgG4 heavy chain and rhesus kappa light chain constant region sequences.

Recombinant heavy and light chains were subcloned into expression vectors and packaged in retroviral vectors used to transduce Chinese hamster ovary cells using the GPEx™ expression technology (Catalent Pharma Solutions, Middleton, Wis.). A pool of transduced cells was grown in serum-free medium and secreted antibody was purified by protein A affinity chromatography. The purified chimeric rhesus IgG1 (2C10R1, 3A8R1) and IgG4 (2C10R4) antibodies were diafiltered into phosphate buffer; endotoxin levels were confirmed to be less than 1 endotoxin unit/mg.

Antibody Characterization

2C10 Binds to CD40 and Prevents Binding of CD154

To assess the ability of 2C10 to bind to both rhesus and human CD40, recombinantly expressed human or rhesus CD40 were adsorbed to ELISA plates and reacted with varying concentrations of 2C10. Binding of 2C10 to CD40 was detected using goat anti-mouse IgG-HRP in an ELISA. The results in FIG. 2B show that 2C10 have similar binding affinities to rhesus and human CD40, which is important for clinical translation of 2C10. To confirm the ability of 2C10 to block binding of its cognate ligand, CD154, rhesus and human B cells were incubated with escalating concentrations of 2C10 or an isotype control and then incubated with histidine-tagged soluble CD154 (R&D Systems, Minneapolis, Minn.) and analyzed for histidine expression. 2C10 blocked the binding of CD154 in a dose-dependent manner (FIG. 3), indicating that 2C10 can effectively block the interaction of T cell-bound CD154 with CD40 on B cells and antigen-presenting cells.

2C10 Blocks B Cell Activation in Rhesus Monkey and Human Peripheral Blood Mononuclear Cells The CD40 antibody 2C10 was characterized with respect to its ability to affect B cell activation both using rhesus monkey and human peripheral blood mononuclear cells (PBMCs). CD20 expression was chosen as being an indicator of B cells, and expression of CD23, CD80, and CD86 is associated with B cell activation. 2C10 was first assessed for its ability to bind to CD20. Rhesus or human PBMCs were incubated with fluorochrome-conjugated 2C10 and an anti-CD20 antibody. Flow cytometric analysis was used to confirm the binding of 2C10 to human and rhesus CD20+ B cells (FIG. 2A). In another set of experiments, PBMCs from either rhesus monkey or humans were cultured either in the presence or absence of CD154$^+$ Jurkat D1.1 cells, an immortalized T lymphocyte cell line. Activation of B cells was determined by measuring expression of three markers (CD23, CD80, and CD86) in CD20$^+$ cells present in the PBMCs. The general scheme of this assay is shown in FIG. 4. As shown in FIG. 4, culturing PBMCs in the presence of Jurkat cells resulted in increased expression of all three markers, indicating that B cells are activated by the CD154$^+$ Jurkat cells.

To test the ability of antibodies to block B cell activation, PBMCs and Jurkat cells were co-cultured in the presence or absence of one of three antibodies: 3A8, 5C8, and 2C10. The 3A8 antibody is a mouse anti-human CD40 antibody (ATCC Deposit No. HB-12024), and 5C8 is an anti-CD154 antibody (ATCC Deposit No. CRL-10915). Each was used as a positive control. Co-cultures were conducted over a range of five orders of magnitude of antibody concentration (0.001 µg to 10 µg). As shown in FIG. 5, 3A8 did not block B cell activation in rhesus PBMCs, as measured by CD23 expression, whereas both 2C10 and 5C8 were able to block activation with similar efficiency. Corresponding changes were also observed with CD80 and CD86 expression. These results indicate that 2C10 binds to a different epitope on CD40 than 3A8. These results also indicate that 2C10 acts primarily as a CD40 antagonist in contrast to 3A8 which has previously been shown to act as partial agonists with weak stimulatory potential (Adams et al., *J. Immunol.* 174:542-50, 2005, Badell et al., *Am. J. Transplant.* accepted for publication, 2011). When a similar experiment was performed using human, rather than rhesus, PBMCs, both 2C10 and 5C8 were again observed to block B cell activation, as measured by CD86 expression, with similar efficiency. Here, the 3A8 antibody, unlike with the rhesus PBMCs, blocked B cell activation (FIG. 6).

The 2C10 and 3A8 antibodies were also tested for their ability to activate B cells in the absence of Jurkat cells using either rhesus monkey or human PBMCs. Here, PBMCs were cultured either in the presence or absence of either 2C10 or 3A8. Expression of CD23, CD80, and CD86 was then measured in CD20$^4$ cells. As shown in FIG. 7, CD23 expression in rhesus cells was increased in the presence of the 3A8, but not the 2C10, antibody. By contrast, neither 3A8 nor 2C10 activated human B cells. The differences in activity observed between the 3A8 and 2C10 antibody indicate that the 2C10 antibody binds to an epitope different from that of the 3A8 antibody.

2C10 Prevents a T Cell-dependent Antibody Response

Having established that 2C10 binds to a unique epitope on CD40, inhibits B cell activation similarly to an anti-CD154 antibody, and lacks agonistic properties, we then characterized the effects of 2C10 in vivo. Recombinant mouse-rhesus chimeric forms of 2C10 were generated using either rhesus IgG1 (2C10R1) or IgG4 (2C10R4) heavy chain and rhesus kappa light chain constant region sequences. A chimeric rhesus IgG1 form of 3A8 (3A8R1) was also generated for use as a control.

Rhesus macaques were immunized once on day zero with 4-hydroxy-3-nitrophenylacetyl-conjugated keyhole limpet hemocyanin (KLH, 10 mg IM) antigen (Biosearch Technologies, Novato, Calif.). Prior to immunization and at one week, cohorts of three animals received an intravenous dose (50 mg/kg) of 2C10R1, 2C10R4, 3A8R1, or saline. All animals were observed for 70 days, and flow cytometry was performed weekly. Treatment with either recombinant 2C10 isotypes resulted in modest change in peripheral B cell counts (FIG. 8) compared to the previously reported significant and prolonged depletion of peripheral B cells occurring in animals receiving either 3A8R1 (Badell et al., *Am. J. Transplant.* 10:214, 2010) or Chi220 (Adams et al., *J. Immunol.* 174:542-50, 2005).

T cell-dependent antibody responses to KLH-NP were tested by ELISA. Plates were coated with KLH (0.01 mg/ml, Sigma, St. Louis, Mo.) and blocked with Super Block (Thermo Scientific, Woodstock, Ga.). Pre- and post-treatment plasma samples were serially diluted, plated for 1 hr, and washed with phosphate-buffered saline/0.05% Tween. Anti-KLH antibodies were detected by incubating for 1 hr with monoclonal anti-rhesus IgG-horseradish peroxidase (clone 1B3, NHP Reagent Resource, Boston, Mass.). Plates were then incubated with Peroxidase Substrate Solution (KPL). Stop solution (KPL) was then added, and optical density was read on an ELISA plate reader at 450 nm. A sample was considered positive at a given dilution if the optical density reading of the post-treatment plasma exceeded the optical density of the pre-treatment plasma at the same dilution by 2-fold. Following KLH immunization, control animals developed high-titer KLH-specific IgG (FIG. 9). Animals that received 3A8R1 also developed anti-KLH responses, but titers were approximately 10-fold lower than controls despite significant depletion of B cells. In contrast, the generation of IgG anti-KLH antibodies was nearly completely blocked through day 56 in all animals that received either 2C10R1 or 2C10R4.

2C10 Significantly Prolongs Islet Allograft Survival in a Macaque Model of Allogeneic Islet Transplantation We further tested 2C10R4, the CD4 purified chimeric rhesus IgG4 antibody, in a nonhuman primate allogenic islet transplant model (FIG. 10). Rhesus macaques weighing 10-20 kg underwent donor pancreatectomy one day prior to transplantation via a midline laparotomy. The pancreas was isolated and placed on ice after the animals were terminally exsanguinated. Islet isolation was performed using Collagenase/Neutral protease (950 Wunsch units and 63 units, respectively; Serva, Heidelberg, Germany). The digested pancreas was purified on a four layer, discontinuous Euroficoll gradient (Mediatech, Manassas, Va.) and Cobe 2991 blood cell processor (CaridianBCT, Lakewood, Colo.). Samples of the final islet preparation were counted and expressed as islet equivalents (IEQ). Isolated islets were cultured overnight, counted and suspended in Transplant Media (Mediatech).

Rhesus macaques weighing 3-5 kg were rendered diabetic using streptozotocin (1250 mg/m$^2$ IV; Zanosar, Teva Parenteral Medicines, Irvine, Calif.) four weeks prior to transplantation. Diabetes was confirmed by intravenous glucose tolerance test (IVGTT) with a 500 mg/kg bolus of dextrose and measurement of primate C-peptide. Glucose levels were monitored and C-peptide was measured at baseline and 10, 30, 60 and 90 after injection of dextrose. Diabetes was confirmed by measurement of elevated blood glucose levels in the absence of detectable serum C-peptide. Diabetic recipients underwent MHC-mismatched islet allotransplantation. A mean of 15,745 (+4,063) IEQ were infused via a small midline laparotomy and cannulation of a mesenteric vein.

Blood glucose levels were measured twice daily by earstick; NPH (Novolin; Novo Nordisk, Princeton, N.J.) and glargine (Lantus; Sanofi-Aventis, Bridgewater, N.J.) insulin were administered to maintain fasting blood glucose (FBG) less than 300 mg/dL pre-transplant and following graft rejection. IVGTT was performed periodically post-transplant to monitor graft function. Transplant recipients underwent weekly flow cytometric analysis to monitor T cell (CD3 V450, CD4 PerCP-Cy5.5, CD8 PerCp; BD Bioscience) and B cell (CD20 PE, BD Bioscience) populations. After islet engraftment rejection was defined as FBG greater than 130 mg/dL on two consecutive days. Primary endpoint was rejection-free islet graft survival. All animals used in these experiments were treated in compliance with the Emory University IACUC and the Guide for the Care and Use of Laboratory Animals.

Transplant recipients received either 2C10R4, basiliximab (Simulect, Novartis, Basel, Switzerland) and sirolimus, or basiliximab and sirolimus alone. 2C10R4 (50 mg/kg) was administered intravenously on post-operative day (POD) 0 and 7. Basiliximab (0.3 mg/kg) was administered intravenously on POD 0 and 3. Sirolimus was administered intramuscularly daily to achieve trough levels of 5-15 ng/ml through POD 120. All three animals receiving basiliximab and sirolimus alone are historic controls (Badell et al., *J. Clin. Invest.* 120:4520-312, 2010). Two of these historic controls (RQz6 and RIb7) underwent diabetes induction by pancreatectomy and received oral sirolimus.

Treatment with the regimens described above resulted in significantly prolonged islet graft survival (FIG. 11A) compared to controls receiving only basiliximab induction and sirolimus maintenance therapy (FIG. 11B). Median rejection-free graft survival time for animals receiving 2C10R4 is 280 days compared to 8 days for control animals (p=0.010, Table 1). Pharmacokinetic data predict that plasma 2C10R4 levels would be less than 1 µg/ml by POD 100. Because sirolimus was discontinued at POD120, the recipient with the longest survival (304 days) received no immunosuppression for approximately 24 weeks prior to rejection. No animals treated with 2C10R4 developed clinically relevant infectious complications or weight loss. These results reflect animals that received the IgG4 isotype of 2C10. Two additional animals that received the IgG1 isotype of 2C10 (2C10R1) in combination with basiliximab and sirolimus achieved similarly prolonged graft survival of 220 and 162 days (data not shown). Given the positive results with 2C10 used as induction therapy, the next step is to assess the effects on graft survival by administering 2C10 as maintenance therapy.

TABLE 1

| Recipient | Therapy | IEQ/kg | Graft Survival (days) | Comment |
|---|---|---|---|---|
| DP4A | 2C10R4/Basiliximab/Sirolimus | 21,973 | 296 | Rejection |
| RAo13 | 2C10R4/Basiliximab/Sirolimus | 14,388 | 304 | Rejection |
| RZq13 | 2C10R4/Basiliximab/Sirolimus | 15,881 | 265 | Rejection |
| RRq13 | 2C10R4/Basiliximab/Sirolimus | 20,596 | 163 | Rejection |
| RQz6 | Basiliximab/Sirolimus | 12,980 | 8 | Rejection |
| RIb7 | Basiliximab/Sirolimus | 10,903 | 8 | Rejection |
| RMc11 | Basiliximab/Sirolimus | 13,796 | 10 | Rejection |

Blockade of the CD40/CD154 Pathway in Conjunction with the CD28/B7 Pathway

Blockade of the CD40/CD154 pathway may prove useful in conjunction with other costimulation blockade agents. Belatacept, a high affinity version of CTLA4-Ig designed to block the CD28/B7 costimulatory pathways, has shown efficacy in nonhuman primate models of renal and islet transplantation and in phase II and III clinical trials in renal transplantation (Larsen et al., *Transplantation* 90:1528-35, 2010, Vincenti et al., *Am. J. Transplant.* 10:535-46, 2010, Adams et al., *J. Immunol.* 174:542-50, 2005, Adams et al., *Diabetes* 51:265-70, 2002, Larsen et al., *Am. J. Transplant.* 5:443-53, 2005, Vincenti et al., *N. Engl. J. Med.* 358:770-81, 2005). The BENEFIT trial revealed superior renal function in patients treated with belatacept; however, these patients had a higher incidence and more severe grade of biopsy-proven acute rejection (Larsen et al., *Transplantation* 90:1528-35, 2010, Vincenti et al. *Am. J. Transplant.* 10:535-46, 2010). In light of this increased rate of acute rejection and the synergy between CD40 and B7 blockade (Larsen et al., *Nature* 381:434-8, 1996), we next want to test the efficacy of combined 2C10 and belatacept therapy in non-human primate kidney transplantation.

Epitope Mapping

Methods for identifying the particular epitope to which an antibody binds are known to those skilled in the art. Standard techniques include peptide scanning, in which overlapping, short peptides (for example, 10-30 amino acids, e.g., 20, in length) derived from the full length protein to which the antibody binds are individually tested for their ability to bind the antibody. From such experiments, the region of the protein to which the antibody binds can then be determined.

Site-directed mutagenesis can also be used to identify the antigenic region(s) of a particular protein. In this approach, point mutations are systematically introduced into the target polypeptide and the ability of the antibody to bind the peptide with mutations at various positions is used to determine whether a particular region of that protein contains the epitope to which the antibody binds.

Antibody epitopes can also be identified using high-through mutagenesis techniques, such as Shotgun Mutagenesis (Integral Molecular, Inc., Philadelphia, Pa.), which can be used to generate large numbers of mutations within the target protein. Such methodologies permit efficient identification of eptitopes within the protein.

To determine if various antibodies to CD40 bind similar epitopes, an in vitro competitive blockade assay was performed. The antibodies 2C10, 3A8 and Chi220, a chimeric IgG1 CD40-specific antibody, were used in the assay. 2C10 was conjugated to allophycocyanin (APC) using the Lightning Link antibody labeling kit (Novus Biologics, Littleton, Colo.). Human PBMCs were incubated with escalating concentrations of 2C10, 3A8, or Chi220, and then stained with the APT-conjugated 2C10 to assess the ability of each antibody to cross-block 2C10. Binding of APC-conjugated 2C10 decreased with increasing concentrations of 2C10 but not Chi220 or 3A8 as shown in FIG. 12. The result indicates that 2C10 binds a unique epitope distinct from either Chi220 or 3A8.

Generation of Additional Antibodies

Additional antibodies (e.g., monoclonal, polyclonal, polyspecific, or mono-specific antibodies) against the CD40 epitope recognized by 2C10 can be made, e.g., using any of the numerous methods for making antibodies known in the art. In one example, a coding sequence for an eptiope recognized by the 2C10 antibody is expressed as a C-terminal fusion with glutathione S-transferase (GST) (Smith et al., *Gene* 67:31-40, 1988). The fusion protein is purified on glutathione-Sepharose beads, eluted with glutathione, cleaved with thrombin (at an engineered cleavage site), and purified for immunization of rabbits. Primary immunizations are carried out with Freund's complete adjuvant and subsequent immunizations with Freund's incomplete adjuvant. Antibody titers are monitored by Western blot and immunoprecipitation analyses using the thrombin-cleaved protein fragment of the GST fusion protein. Immune sera are affinity purified using CNBr-Sepharose-coupled protein. Antiserum specificity can be determined using a panel of unrelated GST proteins.

As an alternate or adjunct immunogen to GST fusion proteins, peptides corresponding to relatively unique immunogenic regions of a polypeptide of the invention can be generated and coupled to keyhole limpet hemocyanin (KLH) through an introduced C-terminal lysine. Antiserum to each of these peptides is similarly affinity purified on peptides conjugated to BSA, and specificity is tested by ELISA or Western blot analysis using peptide conjugates, or by Western blot or immunoprecipitation using the polypeptide expressed as a GST fusion protein.

Alternatively, monoclonal antibodies that specifically bind the CD40 eptiope recognized the 2C10 antibody can be prepared using standard hybridoma technology (see, e.g., Kohler et al., *Nature* 256:495-7, 1975; Kohler et al., *Eur. J. Immuno.* 6:511-9, 1976; Kohler et al., *Eur. J. Immunol.* 6:292-5, 1976; Hammerling et al., *Monoclonal Antibodies and T Cell Hybridomas*, Elsevier, N Y, 1981). Once produced, monoclonal antibodies can also be tested for specific recognition by Western blot or immunoprecipitation analysis. Alternatively, monoclonal antibodies can be prepared using the polypeptide of the invention described above and a phage display library (Vaughan et al., *Nat. Biotechnol.* 14:309-14, 1996).

Epitopic fragments can be generated by standard techniques, e.g., using PCR and cloning the fragment into a pGEX expression vector. Fusion proteins are expressed in *E. coli* and purified using a glutathione agarose affinity matrix. To minimize potential problems of low affinity or specificity of antisera, two or three such fusions are generated for each protein, and each fusion is injected into at least two rabbits. Antisera are raised by injections in a series, and can include, for example, at least three booster injections.

In order to generate polyclonal antibodies on a large scale and at a low cost an appropriate animal species can be chosen. Polyclonal antibodies can be isolated from the milk or colostrum of, e.g., immunized cows. Bovine colostrum contains 28 g of IgG per liter, while bovine milk contains 1.5 g of IgG per liter (Ontsouka et al., *J. Dairy Sci.* 86:2005-11, 2003). Polyclonal antibodies can also be isolated from the yolk of eggs from immunized chickens (Sarker et al., *J. Pediatr. Gastroenterol. Nutr.* 32:19-25, 2001).

Multiple adjuvants are approved for use in dairy cows. Adjuvants useful in this invention include, but are not limited to, Emulsigen®, an oil-in-water emulsified adjuvant, Emulsigen®-D, an oil-in-water emulsified adjuvant with DDA immunostimulant, Emulsigen®-P, an oil-in-water emulsified adjuvant with co-polymer immunostimulant, Emulsigen®-BCL, an oil-in-water emulsified adjuvant with block co-polymer immunostimulant, Carbigen™, a carbomer base, and Polygen™, a co-polymer base. All of the listed adjuvants are commercially available from MVP Laboratories in Omaha, Nebr.

Useful antibodies can be identified in several different screening assays. First, antibodies are assayed by ELISA to determine whether they are specific for the immunizing antigen (i.e., the CD40 epitope described herein). Using standard techniques, ELISA plates are coated with immunogen, the antibody is added to the plate, washed, and the presence of bound antibody detected by using a second antibody specific for the Ig of the species in which the antibody was generated.

A functional in vitro assay can be used to screen antibodies e.g., an neutralizing assay based on monocyte-derived dendritic cells.

Direct measurements of bovine immunoglobulin in illeal fluid in human subjects have shown that significant amounts of immunoglobulin survive transit through the stomach and small intestine (Warny et al., *Gut* 44:212-7, 1999). Methods have also been described to formulate avian immunoglobulin (IgY) for GI delivery (Kovacs-Nolan et al., *Immunol. Methods* 296:199-209, 2005).

Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature* 321:522-5, 1986; Riechmann et al., *Nature* 332:323-7, 1988; Verhoeyen et al., *Science* 239:1534-6, 1988), by substituting hypervariable region sequences for the corresponding sequences of a human antibody. Accordingly, such "humanized" antibodies are chimeric antibodies (U.S. Pat. No. 4,816,567), where substantially less than an intact human variable domain has been substituted by the corresponding sequence from a non-human species. In practice, humanized antibodies are typically human antibodies in which at least some hypervariable region residues as well as other variable region residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al., *J. Immunol.* 151:2296-308, 1993; Chothia et al., *J. Mol. Biol.* 196:901-17, 1987. Another method uses a particular framework derived from the consensus sequence of all human antibodies of a particular subgroup of light or heavy chains. The same framework may be used for several different humanized antibodies. See, e.g., Carter et al., *Proc. Natl. Acad. Sci. USA* 89:4285-9, 1992; Presta et al., *J. Immunol.* 151:2623-32, 1993.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human antibodies of the invention can be constructed by combining Fv clone variable domain sequence(s) selected from human-derived phage display libraries with known human constant domain sequences(s) (Hoogenboom et al., *J. Mol. Biol.* 227:381-8, 1992; Marks et al., *J. Mol. Biol.* 222:581-97, 1991). Alternatively, human monoclonal antibodies of the invention can be made by the hybridoma method. Human myeloma and mouse-human heteromyeloma cell lines for the production of human monoclonal antibodies have been described, for example, by Kozbor, *J. Immunol.* 133:3001-5, 1984; Brodeur et al., *Monoclonal Antibody Production Techniques and Applications*, pp. 51-63 (Marcel Dekker, Inc., New York, 1987); and Boerner et al., *J. Immunol.* 147: 86-95, 1991.

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA* 90:2551-5, 1993; Jakobovits et al., *Nature* 362:255-8, 1993; Brüggemann et al., *Year Immunol.* 7:33-40, 1993.

Gene shuffling can also be used to derive human antibodies from non-human, e.g., rodent, antibodies, where the human antibody has similar affinities and specificities to the starting non-human antibody. According to this method, which is also called "epitope imprinting," either the heavy or light chain variable-region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab where the human chain restores the antigen binding site destroyed upon removal of the corresponding non-human chain in the primary phage display clone, i.e., the epitope governs (imprints) the choice of the human chain partner. When the process is repeated in order to replace the remaining non-human chain, a human antibody is obtained (see PCT Publication WO 93/06213). Unlike traditional humanization of non-human antibodies by CDR grafting, this technique provides completely human antibodies, which have no FR or CDR residues of non-human origin.

Antibody Fragments

The invention also features antibody fragments that comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

Fv is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs) of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

Single-chain Fv or scFv antibody fragments comprise the $V_H$ and $V_L$ domains of antibody, where these domains are present in a single polypeptide chain. Generally, the scFv polypeptide further comprises a polypeptide linker between the $V_H$ and $V_L$ domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

Diabodies are antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, European Patent No. 404,097; PCT Publication WO 1993/01161; Hudson et al., *Nat. Med.* 9:129-34, 2003; and Hollinger et al., *Proc. Natl. Acad. Sci. USA* 90:6444-8, 1993. Triabodies and tetrabodies are also described in Hudson et al., *Nat. Med.* 9:129-34, 2003.

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. *Nat. Med.* 9:129-134, 2003.

Various techniques have been developed for the production of antibody fragments. Traditionally, these fragments were derived via proteolytic digestion of intact antibodies (see, e.g., Morimoto et al., *J. Biochem. Biophys. Methods* 24:107-17, 1992; and Brennan et al., *Science* 229:81-3, 1985). However, these fragments can now be produced directly by recombinant host cells. Fab, Fv, and ScFv antibody fragments can all be expressed in and secreted from *E. coli*, thus allowing the facile production of large amounts of these fragments. Antibody fragments can be isolated from the antibody phage libraries. Alternatively, Fab'-SH fragments can be directly recovered from *E. coli* and chemically coupled to form $F(ab')_2$ fragments (Carter et al., *Bio/Technology* 10:163-7, 1992). In another approach, $F(ab')_2$ fragments are isolated directly from recombinant host cell culture. Fab and $F(ab')_2$ fragment with increased in vivo half-life comprising salvage receptor binding epitope residues are described in U.S. Pat. No. 5,869,046. Other techniques for the production of antibody fragments will be apparent to the skilled practitioner.

Pharmaceutical Compositions

The present invention provides a composition, e.g., a pharmaceutical composition, containing an antibody, or antigen-binding portion(s) thereof, of the present invention, formulated together with a pharmaceutically acceptable carrier. Pharmaceutical compositions of the invention also can be administered in combination therapy, i.e., combined with other agents (e.g., immunosuppressants). As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intrathecal, intramuscular, subcutaneous, parenteral, spinal or epidermal administration (e.g., by injection or infusion). Depending on the route of administration, the antibodies of the invention may be coated in a material to protect the compound from the action of acids and other natural conditions that may inactivate the compound.

A composition of the present invention can be administered by a variety of methods known in the art. As will be appreciated by the skilled artisan, the route and/or mode of administration will vary depending upon the desired results. Administration may be parenteral, intravenous, intrathecal, subcutaneous, oral, topical, or local, for example, by direct injection into the cerebrospinal fluid. Intravenous delivery by continuous infusion is one exemplary method for administering the therapeutic antibodies of the present invention. The therapeutic compound may be in the form of a solution; a suspension, an emulsion, an infusion device, or a delivery device for implantation, or it may be presented as a dry powder to be reconstituted with water or another suitable vehicle before use. The composition can be in the form of a pill, tablet, capsule, liquid, or sustained release tablet for oral administration; or a liquid for intravenous, intrathecal, subcutaneous or parenteral administration; or a polymer or other sustained release vehicle for local administration.

Methods well known in the art for making formulations are found, for example, in "Remington: The Science and Practice of Pharmacy" (20th ed., ed. A. R. Gennaro Ark., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful delivery systems include ethylene-vinyl acetate copolymer particles, osmotic pumps, intrathecal pumps, implantable infusion systems, and liposomes. The concentration of the compound in the formulation varies depending upon a number of factors, including the dosage of the drug to be administered, and the route of administration.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 7:27-41, 1984). Pharmaceutically acceptable carriers include sterile aqueous solutions or dispersions and sterile powders for the extemporaneous preparation of sterile injectable solutions or dispersion. The use of such media and agents for pharmaceutically active substances is known in the art and is included in the invention except where any conventional media or agent is incompatible with the active compound. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the antibodies of the invention may be administered once or twice weekly by subcutaneous injection or once or twice monthly by subcutaneous injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Compositions of the invention may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin. When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

For intravenous or intrathecal delivery or direct injection, the composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian can start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. Examples of well-known implants, delivery systems, and modules useful in the present invention are known to those skilled in the art.

Conditions and Disorders

The antibodies and antibody fragments described herein may be used in any situation in which immunosuppression is desired (e.g., transplant rejection or autoimune disorders). These antibodies are particularly useful for treating transplant rejection, e.g., reducing the likelihood that a particular transplant is rejected by the host or increasing the time before rejection takes place. The antibodies described herein can be used in conjunction with transplantation of any organ or any tissue that is suitable for transplantation. Exemplary organs include heart, kidney, lung, liver, pancreas, intestine, and thymus; exemplary tissues include bone, tendon, cornea, skin, heart valve, vein, and bone marrow.

The antibodies and antibody fragments can also be used to treat autoimmune disorders, particular disorders where autoantibodies are implicated in the pathogenesis of the disease. Autoimmune diseases that are or can be associated with autoantibody production include systemic lupus erythematosus (SLE), CREST syndrome (calcinosis, Raynaud's syndrome, esophageal dysmotility, sclerodactyl, and telangiectasia), opsoclonus, inflammatory myopathy (e.g., polymyositis, dermatomyositis, and inclusion-body myositis), systemic scleroderma, primary biliary cirrhosis, celiac disease (e.g., gluten sensitive enteropathy), dermatitis herpetiformis, Miller-Fisher Syndrome, acute motor axonal neuropathy (AMAN), multifocal motor neuropathy with conduction block, autoimmune hepatitis, antiphospholipid syndrome, Wegener's granulomatosis, microscopic polyangiitis, Churg-Strauss syndrome, rheumatoid arthritis, chronic autoimmune hepatitis, scleromyositis, myasthenia gravis, Lambert-Eaton myasthenic syndrome, Hashimoto's thyroiditis, Graves' disease, Paraneoplastic cerebellar degeneration, Stiff person syndrome, limbic encephalitis, Isaacs Syndrome, Sydenham's chorea, pediatric autoimmune neuropsychiatric disease associated with *Streptococcus* (PANDAS), encephalitis, diabetes mellitus type 1, and Neuromyelitis optica.

Other autoimmune disorders include pernicious anemia, Addison's disease, psoriasis, inflammatory bowel disease, psoriatic arthritis, Sjögren's syndrome, lupus erythematosus (e.g., discoid lupus erythematosus, drug-induced lupus erythematosus, and neonatal lupus erythematosus), multiple sclerosis, and reactive arthritis.

Additional disorders that may be treated using the methods of the present invention include, for example, polymyositis, dermatomyositis, multiple endocrine failure, Schmidt's syndrome, autoimmune uveitis, adrenalitis, thyroiditis, autoimmune thyroid disease, gastric atrophy, chronic hepatitis, lupoid hepatitis, atherosclerosis, presenile dementia, demyelinating diseases, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, alopecia arcata, pemphigoid, scleroderma, progressive systemic sclerosis, adult onset diabetes mellitus (e.g., type II diabetes), male and female autoimmune infertility, ankylosing spondolytis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, endocarditis, endomyocardial fibrosis, endophthalmitis, erythema elevatum et diutinum, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and non-Hodgkin's lymphoma, renal cell carcinoma, multiple myeloma, Eaton-Lambert syndrome, relapsing polychondritis, malignant melanoma, cryoglobulinemia, Waldenstrom's macroglobulinemia, Epstein-Barr virus infection, mumps, Evan's syndrome, and autoimmune gonadal failure.

Immunosuppressants

The antibodies and antibody fragments described herein can be formulated or administered in combination with an immunosuppressant. Examples of immunosuppressants include, but are not limited to, calcineurin inhibitors (e.g., cyclosporin A (Sandimmune®), cyclosporine G tacrolimus (Prograf®, Protopic®)), mTor inhibitors (e.g., sirolimus (Rapamune®, Neoral®), temsirolimus (Torisel®), zotarolimus, and everolimus (Certican®)), fingolimod (Gilenya™), myriocin, alemtuzumab (Campath®, MabCampath®, Campath-1H®), rituximab (Rituxan®, MabThera®), an anti-CD4 monoclonal antibody (e.g., HuMax-CD4), an anti-LFA1 monoclonal antibody (e.g., CD11a), an anti-LFA3 monoclonal antibody, an anti-CD45 antibody (e.g., an anti-CD45RB antibody), an anti-CD19 antibody (see, e.g., U.S. Patent Publication 2006/0280738), monabatacept (Orencia®), belatacept, indolyl-ASC (32-indole ether derivatives of tacrolimus and ascomycin), azathioprine (Azasan®, Imuran®), lymphocyte immune globulin and anti-thymocyte globulin [equine] (Atgam®), mycophenolate mofetil (Cellcept®), mycophenolate sodium (Myfortic®), daclizumab (Zenapax®), basiliximab (Simulect®), cyclophosphamide (Endoxan®, Cytoxan®, Neosar™, Procytox™, Revimmune™), prednisone, prednisolone, leflunomide (Arava®), FK778, FK779, 15-deoxyspergualin (DSG), busulfan (Myleran®, Busulfex®), fludarabine (Fludara®), methotrexate (Rheumatrex®, Trexall®), 6-mercaptopurine (Purinethol®), 15-deoxyspergualin (Gusperimus), LF15-0195, bredinin, brequinar, and muromonab-CD3 (Orthoclone®).

Methods for assessing immunosuppressive activity of an agent are known in the art. For example, the length of the survival time of the transplanted organ in vivo with and without pharmacological intervention serves as a quantitative measure for the suppression of the immune response. In vitro assays may also be used, for example, a mixed lymphocyte reaction (MLR) assay (see, e.g., Fathman et al., *J. Immunol.* 118:1232-8, 1977); a CD3 assay (specific activation of immune cells via an anti-CD3 antibody (e.g., OKT3)) (see, e.g., Khanna et al., *Transplantation* 67:882-9, 1999; Khanna et al. (1999) *Transplantation* 67:S58); and an IL-2R assay (specific activation of immune cells with the exogenously added cytokine IL-2) (see, e.g., Farrar et al., *J. Immunol.* 126:1120-5, 1981).

Cyclosporine A (CsA; CAS No. 59865-13-3; U.S. Pat. No. 3,737,433) and its analogs may be used as an immunosuppressant. A number of other cyclosporines and their derivatives and analogs that exhibit immunosuppressive activity are known. Cyclosporines and their formulations are described, for example, in 2004 Physicians' Desk Reference® (2003) Thomson Healthcare, 58th ed., and U.S. Pat. Nos. 5,766,629; 5,827,822; 4,220,641; 4,639,434; 4,289, 851; 4,384,996; 5,047,396; 4,388,307; 4,970,076; 4,990,337; 4,822,618; 4,576,284; 5,120,710; and 4,894,235.

Tacrolimus (FK506) is a macrolide which exerts effects largely similar to CsA, both with regard to its molecular mode of action and its clinical efficacy (Liu, *Immunol. Today* 14:290-5, 1993; Schreiber et al., *Immunol. Today,* 13:136-42, 1992); however, these effects are exhibited at doses that are 20 to 100 times lower than CsA (Peters et al., *Drugs* 46:746-94, 1993). Tacrolimus and its formulations are described, for example, in 2004 Physicians' Desk Reference® (2003) Thomson Healthcare, 58th ed., and U.S. Pat. Nos. 4,894,366; 4,929,611; and 5,164,495.

Sirolimus (rapamycin) is an immunosuppressive lactam macrolide produceable, for example, by *Streptomyces hygroscopicus*. Numerous derivatives of sirolimus and its analogs and their formulations are known and described, for example, in 2004 *Physicians' Desk Reference®* (2003) *Thomson Healthcare,* 58th ed., European Patent EP 0467606; PCT Publication Nos. WO 94/02136, WO 94/09010, WO 92/05179, WO 93/11130, WO 94/02385, WO 95/14023, and WO 94/02136, and U.S. Pat. Nos. 5,023,262; 5,120,725; 5,120,727; 5,177,203; 5,258,389; 5,118,677; 5,118,678; 5,100,883; 5,151,413; 5,120,842; and 5,256,790.

CD40 Fragments

The invention also features fragments of CD40 that include the epitope that is specifically bound by the 2C10 antibody. The 2C10 antibody was raised against the extracellular portion of the CD40 polypeptide; it is thus believed that this antibody reacts with a portion of this sequence (SEQ ID NOS:5 and 6).

The invention therefore features CD40 fragments (e.g., fewer than 150, 120, 100, 80, 70, 60, 50, 40, 30, 20, 18, 15, 12, 11, 10, 9, 8, or 7) amino acids in length that are specifically bound by the 2C10 antibody. In certain embodiments, the fragment is 8-10, 8-12, 8-15, 8-20, 8-30, 8-40, 8-50, 8-60, 8-70, 8-80, or 8-100 amino acids in length. In other embodiments, the fragment is 7-10, 7-12, 7-15, 7-20, 7-30, 7-40, 7-50, 7-60, 7-70, 7-80, or 7-100 in length.

Fusion Proteins

The invention also features fusion protein that includes a fragment described herein and a heterologous sequence. In certain embodiments, one of the fusion partners is the Fc protein (e.g., mouse Fc or human Fc). The fusion may also be a sequence useful for antibody production, e.g., a maltose binding protein or GST. In other embodiments, the fusion protein is a purification or detection tag, for example, proteins that may be detected directly or indirectly such as green fluorescent protein, hemagglutinin, or alkaline phosphatase), DNA binding domains (for example, GAL4 or LexA), gene activation domains (for example, GAL4 or VP16), purification tags, or secretion signal peptides (e.g., preprotyrypsin signal sequence). In other embodiments, the fusion partner may be a tag, such as c-myc, poly histidine, or FLAG. Each fusion partner may contain one or more domains, e.g., a preprotrypsin signal sequence and FLAG tag.

Production of CD40 Fragments and Fusion Proteins

The CD40 fragments and fusion proteins described herein may be produced by transformation of a suitable host cell with a polynucleotide molecule encoding the polypeptide fragment or fusion protein in a suitable expression vehicle.

Those skilled in the field of molecular biology will understand that any of a wide variety of expression systems may be used and that the precise system or host cell used is not critical to the invention. Exemplary expression systems include prokaryotic hosts (e.g., *E. coli*) and eukaryotic hosts (e.g., *S. cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Manassas, Va.). The method of transformation or transfection and the choice of expression vehicle will depend on the host system selected. Transformation and transfection methods are described, e.g., in Kucherlapati et al. (*CRC Crit. Rev. Biochem.* 16:349-379, 1982) and in *DNA Transfer to Cultured Cells* (eds., Ravid and Freshney, Wiley-Liss, 1998); and expression vehicles may be chosen from those provided, e.g., in *Vectors: Expression Systems: Essential Techniques* (ed., Jones, Wiley & Sons Ltd., 1998).

Once the recombinant CD40 polypeptide fragment or fusion protein is expressed, it can be isolated, e.g., using affinity chromatography. In one example, an antibody raised against the fragment or fusion protein (e.g., the 2C10 antibody) may be attached to a column and used to isolate the polypeptide fragment or fusion protein. Lysis and fractionation of fragment- or fusion protein-harboring cells prior to affinity chromatography may be performed by standard methods (see, e.g., *Methods in Enzymology,* volume 182, eds., Abelson, Simon, and Deutscher, Elsevier, 1990).

Once isolated, the CD40 polypeptide fragment or fusion protein can, if desired, be further purified, e.g., by high performance liquid chromatography (see e.g., Fisher, *Laboratory Techniques in Biochemistry and Molecular Biology*, eds., Work and Burdon, Elsevier, 1980; and Scopes, *Protein Purification: Principles and Practice*, Third Edition, ed., Cantor, Springer, 1994).

The CD40 polypeptide fragments or fusion proteins can also be produced by chemical synthesis (e.g., by the methods described in *Solid Phase Peptide Synthesis,* 2nd ed., 1984, The Pierce Chemical Co., Rockford, Ill.; and *Solid-Phase Synthesis: A Practical Guide,* ed., Kates and Albericio, Marcel Dekker Inc., 2000).

OTHER EMBODIMENTS

All patents, patent applications, and publications mentioned in this specification are herein incorporated by reference to the same extent as if each independent patent, patent application, or publication was specifically and individually indicated to be incorporated by reference.

What is claimed is:

1. A polynucleotide encoding an antibody or antigen-binding fragment thereof that specifically binds to an epitope present on CD40, wherein the heavy chain variable region of the antibody or antigen-binding fragment thereof comprises the hypervariable regions set forth in amino acids 20-132 of SEQ ID NO:2, and the light chain variable region of the antibody or antigen-binding fragment thereof comprises the hypervariable regions set forth in amino acids 23-128 of SEQ ID NO:4.

2. The polynucleotide of claim 1, wherein the epitope is present within the sequence of amino acids 8-60 of SEQ ID NO:6.

3. The polynucleotide of claim 1, wherein the antibody or antigen-binding fragment thereof blocks B lymphocyte activation by CD154-expressing Jurkat cells in vitro.

4. The polynucleotide of claim 1, wherein the antibody or antigen-binding fragment thereof inhibits B lymphocyte CD23, CD80, or CD86 expression.

5. The polynucleotide of claim 3, wherein the B lymphocyte is a rhesus B lymphocyte.

6. The polynucleotide of claim 1, wherein the CD40 is rhesus CD40 or human CD40.

7. The polynucleotide of claim 1, wherein the constant regions of the antibody are human constant regions.

8. The polynucleotide of claim 1, wherein the antibody is a humanized antibody or a human antibody.

9. The polynucleotide of claim 1, wherein the antibody is a monoclonal antibody.

10. The polynucleotide of claim 1, wherein the heavy chain variable region of the antibody or antigen-binding fragment thereof comprises amino acids 20-132 of SEQ ID NO:2, and the light chain variable region of the antibody or antigen-binding fragment thereof comprises amino acids 23-128 of SEQ ID NO:4.

11. The polynucleotide of claim 1, wherein the antigen-binding fragment is an antibody that lacks an Fc portion.

12. The polynucleotide of claim 1, wherein the antigen-binding fragment is a F(ab')$_2$, a Fab, an Fv, or an scFv.

13. A vector encoding the polynucleotide of claim 1.

14. A cell comprising the vector of claim 13.

15. The cell of claim 13, wherein said cell is eukaryotic.

16. The cell of claim 14, wherein said cell is mammalian.

17. The cell of claim 13, wherein said cell is prokaryotic.

* * * * *